(12) United States Patent
Shyu et al.

(10) Patent No.: US 10,736,964 B2
(45) Date of Patent: Aug. 11, 2020

(54) IMMUNOMAGNETIC NANOCAPSULE AND KIT FOR TREATING CANCER

(71) Applicant: China Medical University, Taichung (TW)

(72) Inventors: Woei-Cherng Shyu, Taichung (TW); San-Yuan Chen, Hsinchu (TW); Chih-Sheng Chiang, Taichung (TW); Chia-Hung Hsieh, Taichung (TW); Yu-Jung Lin, Taichung (TW); Chang-Hai Tsai, Taichung (TW)

(73) Assignee: China Medical University, Taichung (TW)

(*) Notice: Subject to any disclaimer, the term of this patent is extended or adjusted under 35 U.S.C. 154(b) by 221 days.

(21) Appl. No.: 15/967,579

(22) Filed: Apr. 30, 2018

(65) Prior Publication Data

US 2018/0311354 A1    Nov. 1, 2018

Related U.S. Application Data

(60) Provisional application No. 62/492,525, filed on May 1, 2017.

(30) Foreign Application Priority Data

Jan. 16, 2018   (TW) .............................. 107101583 A

(51) Int. Cl.
*A61K 41/00* (2020.01)
*A61K 47/69* (2017.01)
(Continued)

(52) U.S. Cl.
CPC .......... *A61K 41/0052* (2013.01); *A61B 5/055* (2013.01); *A61K 9/5115* (2013.01);
(Continued)

(58) Field of Classification Search
CPC ................ A61K 47/61; A61K 47/6849; A61K 47/6925; A61K 41/0052; A61K 2039/505;
(Continued)

(56) References Cited

U.S. PATENT DOCUMENTS 5,216,130 A     6/1993  Line et al.
2012/0065158 A1  3/2012  Okamoto et al.
(Continued)

FOREIGN PATENT DOCUMENTS

CN    102716414 A    10/2012
CN    104013640 A     9/2014
(Continued)

OTHER PUBLICATIONS

Chollet, Lucas, et al., "Fucoidans in Nanomedicine", Marine Drugs, vol. 14, Issue 8, Aug. 2016, 1-24.
(Continued)

*Primary Examiner* — Catherine B Kuhlman

(57) ABSTRACT

An immunomagnetic nanocapsule includes a core, a shell and an outer layer. The shell is formed by a complex, and the complex is fabricated by a combination of fucoidan, oxidized dextran, and a plurality of superparamagnetic iron oxide nanoparticles via a hydrophobic interaction. The core is encapsulated in the shell. The outer layer includes at least one antibody immobilized to outside of the shell to form the outer layer, wherein the antibody is an immune checkpoint inhibitor and/or a T cell expansion antibody.

11 Claims, 41 Drawing Sheets
(5 of 41 Drawing Sheet(s) Filed in Color)

(51) Int. Cl.
*A61K 47/61* (2017.01)
*A61K 9/51* (2006.01)
*A61K 38/20* (2006.01)
*A61N 2/02* (2006.01)
*C07K 16/28* (2006.01)
*A61P 35/00* (2006.01)
*A61B 5/055* (2006.01)
*A61N 2/00* (2006.01)
*A61K 47/68* (2017.01)
*A61K 39/00* (2006.01)

(52) U.S. Cl.
CPC .......... *A61K 38/2013* (2013.01); *A61K 41/00* (2013.01); *A61K 47/61* (2017.08); *A61K 47/6849* (2017.08); *A61K 47/6923* (2017.08); *A61K 47/6925* (2017.08); *A61N 2/004* (2013.01); *A61N 2/02* (2013.01); *A61P 35/00* (2018.01); *C07K 16/2809* (2013.01); *C07K 16/2818* (2013.01); *C07K 16/2827* (2013.01); *A61K 2039/505* (2013.01); *C07K 2317/76* (2013.01)

(58) Field of Classification Search
CPC .......... A61K 9/5094; A61K 9/51–5192; A61K 49/1878; A61K 49/1887; A61N 2/00–12; C07K 16/2827; C07K 16/2818
See application file for complete search history.

(56) References Cited

U.S. PATENT DOCUMENTS

2012/0093725 A1* 4/2012 Michel ............... A61K 49/0002
424/1.73
2014/0356421 A1* 12/2014 Chiang .............. A61K 39/3955
424/451
2015/0072946 A1* 3/2015 Ciach .................. C08B 37/0072
514/34
2016/0339091 A1 11/2016 Powell
2017/0252466 A1* 9/2017 Peyman ............... A61K 49/221

FOREIGN PATENT DOCUMENTS

JP 2013536824 A 9/2013
WO 2006091180 A2 8/2006

OTHER PUBLICATIONS

Majidi, Sima, et al., "Current methods for synthesis of magnetic nanoparticles", Artificial Cells, Nanomedicine, and Biotechnology, vol. 44, Issue 2, 2016, 722-734.
Perica, Karlo, et al., "Magnitic Field-Induced T Cell Receptor Clustering by Nanoparticles Enhances T. Cell Activation and Stimulates Antitumor Activity", American Chemical Society, vol. 8, No. 3, 2014, 2252-2260.
Wasiak, Iga, et al., "Dextran Nanoparticle Synthesis and Properties", PloS ONE, vol. 11(1), Jan. 11, 2016, 1-17.
Zhong, Hua, et al., "Overexpression of Hypoxia-indicible Factor 1a in Common Human Cancers and Their Metastases", Cancer Research, vol. 59, Issue 22, Nov. 15, 1999, 5830-5835.
Chiang, Chih-Sheng, et al., "Combination of fucoidan-based magnetic nanoparticles and immunomodulators enhances tumour-localized immunotherapy", Nature Nanotechnology, published in Aug. 2018, vol. 13, issue 8, pp. 746-754.
n
n

* cited by examiner

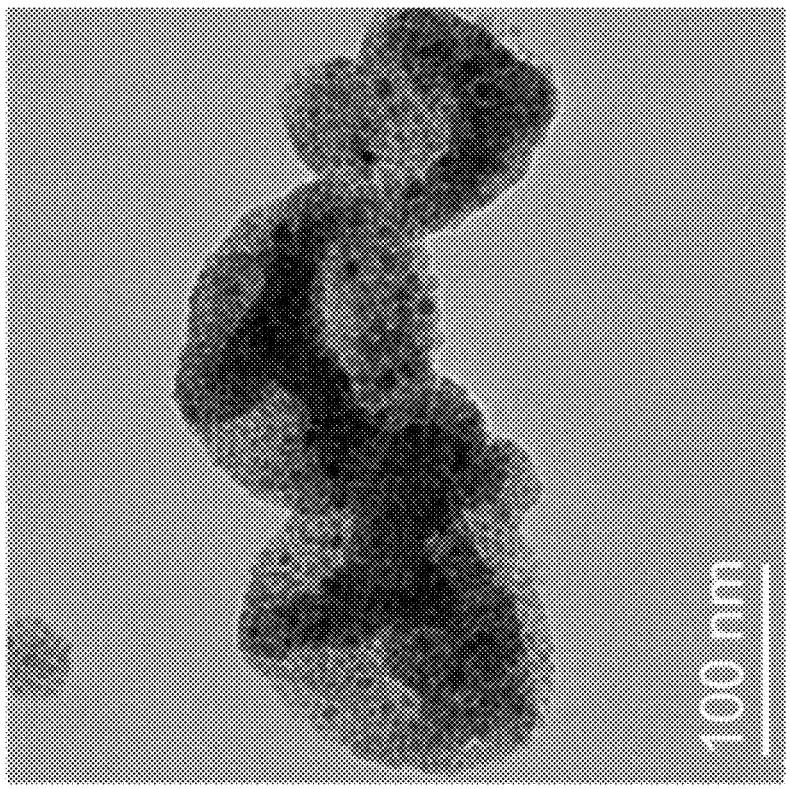
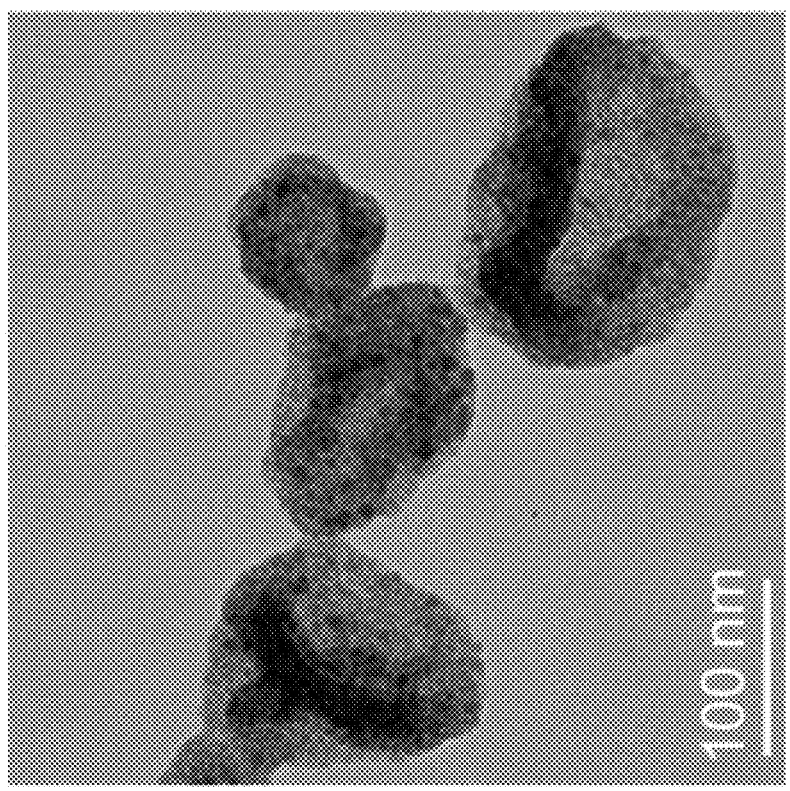
Fig. 7B
Fig. 7A

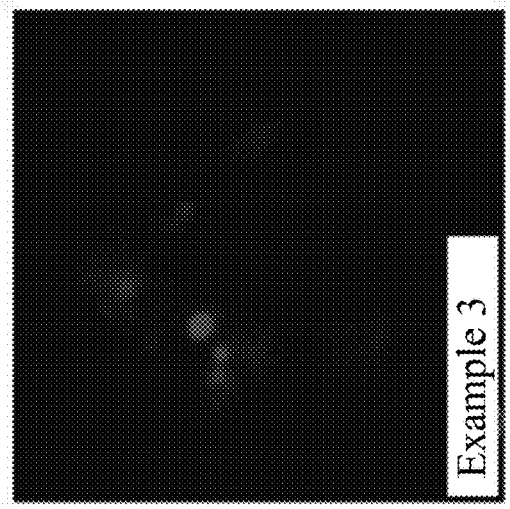
Fig. 12A (Nucleus)
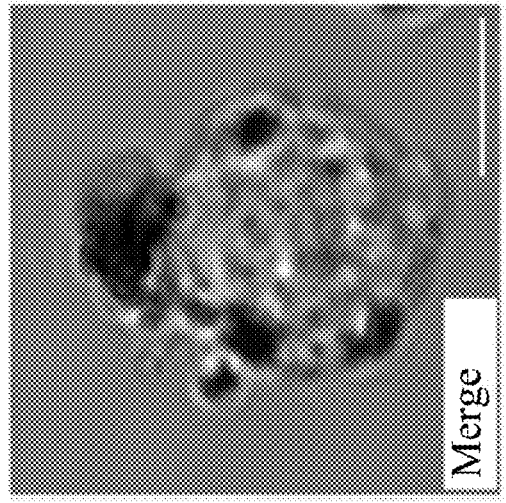
Fig. 12B (Example 3)
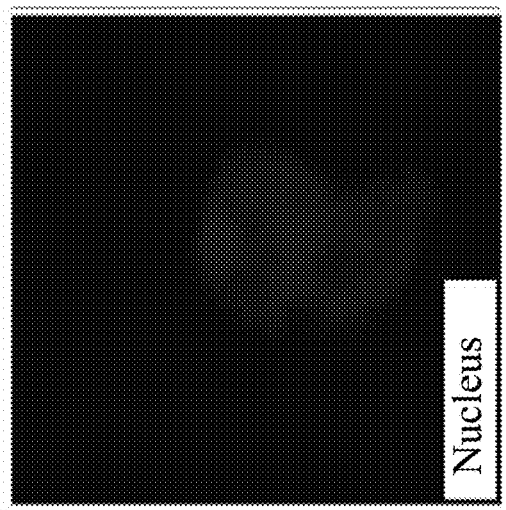
Fig. 12C (Brightfield)
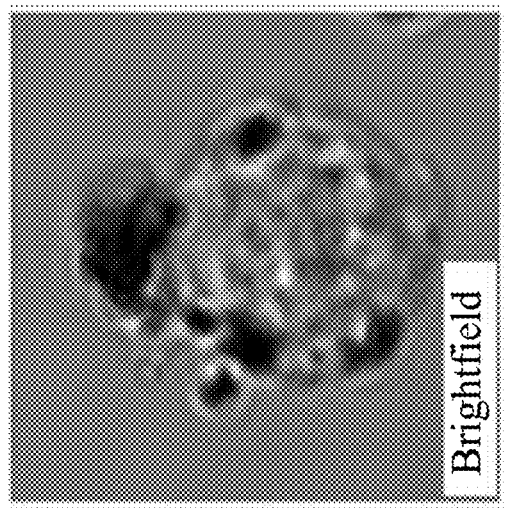
Fig. 12D (Merge)

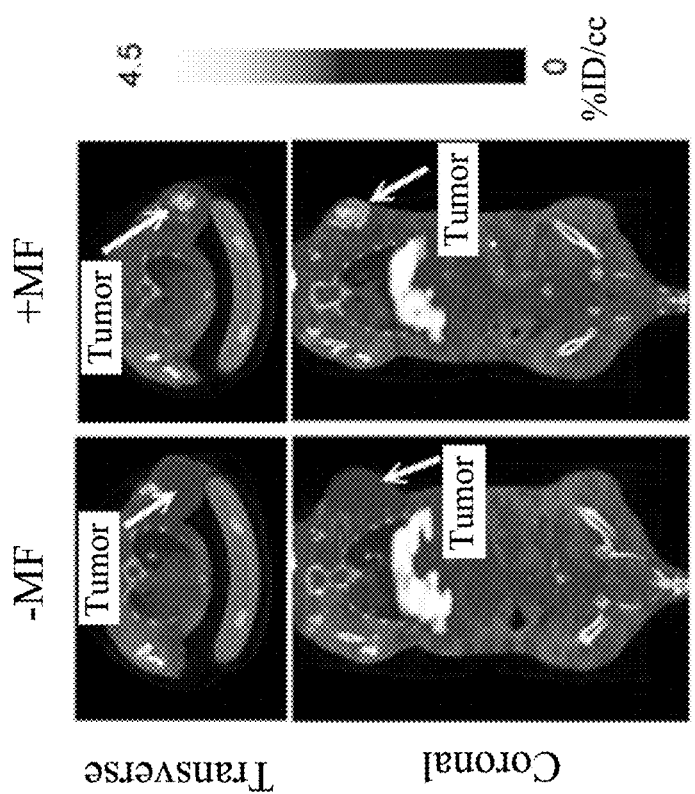
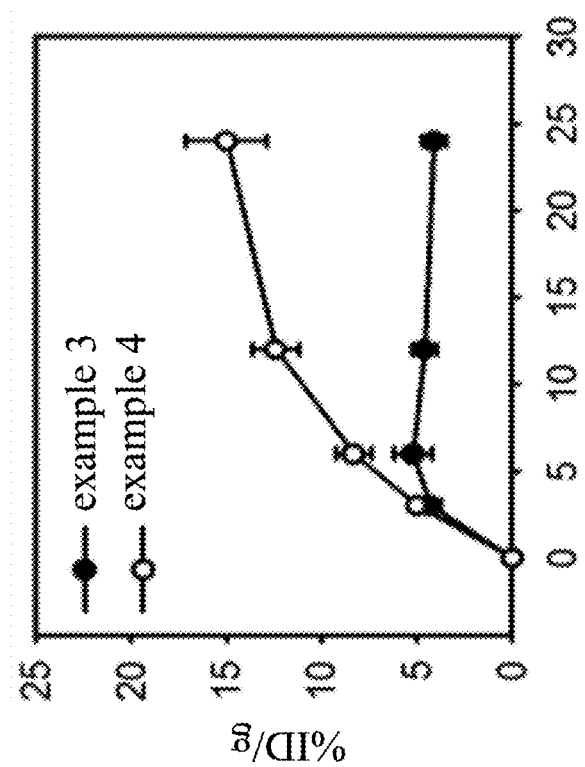
Fig. 13A
Fig. 13B

IMMUNOMAGNETIC NANOCAPSULE AND KIT FOR TREATING CANCER

RELATED APPLICATIONS

This application claims priority to U.S. Provisional Application Ser. No. 62/492,525, filed May 1, 2017, and Taiwan Application Serial Number 107101583, filed Jan. 16, 2018, which are herein incorporated by reference.

BACKGROUND

Technical Field

The present disclosure relates to a composition. More particularly, the present disclosure relates to a medicinal preparation characterized by special physical form.

Description of Related Art

Cancer, also known as malignancy, is a state of abnormal proliferation of cells, and these proliferating cells may invade other parts of the body as a disease caused by a malfunction in the control of cell division and proliferation. The number of people suffering from cancer worldwide has a growing trend. Cancer is one of the top ten causes of death for the Chinese people and has been the top ten causes of death for twenty-seven consecutive years.

Conventional cancer treatments include surgery, radiation therapy, and chemotherapy. Immunotherapy is another method of treating cancer except the above methods. The immune system of the patient is activated in the immunotherapy by using tumor cells or tumor antigens to induce specific cellular and humoral immune responses for enhancing the anti-cancer ability of the patient, preventing the growth, spread, and recurrence of tumors, and achieving the purpose of removing or controlling tumors. The immune checkpoint is one of the most important types of immunotherapy. There have been over 50 clinical trials using immune checkpoint inhibitors combination therapy since 2015. However, the immune checkpoint inhibitor will shut down the feedback mechanism of the human immune system, so that cytotoxic T cells ($CD8^+$ T cells) not only attack cancer cells, but also generate autoimmune reactions such as skin ulcers and gastrointestinal ulcers.

Increasing the immune cells that are specific to tumors in the body is also considered a very promising part of cancer treatment. In most of the current technologies, the immune cells are obtained from tumors of patients and then cultured in vitro. Micron-sized structures (such as microbeads) are used to mimic antigen presenting cells (APCs) for T cell proliferation and training. Finally, the trained immune cells are transferred back into the patient's body to kill cancer cells. However, the above method is time consuming and consumable, and the cancer cells in the patient's body are prone to mutation, so that the returned immune cells lose their effect. On the other hand, microbeads used for proliferation can only be used for in vitro culture due to their large size and cannot be circulated into the target area via human blood. In addition to surface-immobilized antibodies or encapsulated active ingredients in this type of carriers, the carrier-forming material is usually an excipient. The excipient does not contribute much to the therapeutic effect and will limit the administration dose, becoming an inherent defect in this type of carriers.

SUMMARY

According to one aspect of the present disclosure, an immunomagnetic nanocapsule is provided. The immunomagnetic nanocapsule includes a core, a shell and an outer layer. The shell is formed by a complex, and the complex is fabricated by a combination of fucoidan, oxidized dextran, and a plurality of superparamagnetic iron oxide nanoparticles via a hydrophobic interaction. The core is encapsulated in the shell. The outer layer includes at least one antibody immobilized onto outside of the shell to form the outer layer, wherein the antibody is an immune checkpoint inhibitor and/or a T cell expansion antibody.

According to another aspect of the present disclosure, a pharmaceutical composition for treating cancer is provided. The pharmaceutical composition includes the immunomagnetic nanocapsule according to the aforementioned aspect and a pharmaceutically acceptable carrier.

According to yet another aspect of the present disclosure, a kit for treating cancer is provided. The kit includes the immunomagnetic nanocapsule according to the aforementioned aspect and a magnetic field generator.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiments, with reference made to the accompanying drawings as follows:

FIGS. 7A and 7B are transmission electron micrographs of the magnetic fucoidan nanoparticle before and after lyophilized;

FIGS. 12A, 12B, 12C and 12D show cell association ability analysis results of the immunomagnetic nanocapsule of the present disclosure;

FIGS. 13A, 13B and 13C show analysis results of nanomedicine accumulation in tumor of the kit for treating cancer of the present disclosure;

DETAILED DESCRIPTION

A novel immunomagnetic nanocapsule is provided. The immunomagnetic nanocapsule is fabricated by combining a fucoidan, an oxidized dextran, and a plurality of superparamagnetic iron oxide nanoparticles via a hydrophobic interaction and then immobilizing antibody. The fabricated immunomagnetic nanocapsule can markedly improve an anti-cancer effect of immunotherapy with the same antibody alone and can achieve better tumor inhibition with less antibody dosage. A pharmaceutical composition for treating cancer thereof including the immunomagnetic nanocapsule and a pharmaceutically acceptable carrier is also provided. In addition, a kit for treating cancer thereof including the immunomagnetic nanocapsule and a magnetic field generator is provided for enhancing the anti-cancer effect of the immunomagnetic nanocapsule of the present disclosure.

The term "fucoidan" is a water-soluble dietary fiber extracted from sticky and slippery components unique to brown algae. The fucoidan is rich in fucose, is a kind of natural polysaccharide with high biological safety, and has abilities of anti-oxidation, anti-coagulation, anti-thrombosis, anti-virus and anti-cancer.

The term "dextran" is a complex branched glucan (polysaccharide made of many glucose molecules) composed of chains of varying lengths (from 3 Da to 2000 kDa). The straight chain consists of $\alpha$-1,6 glycosidic linkages between glucose molecules, while branches begin from $\alpha$-1,3 linkages. The term "oxidized dextran" is a surface-modified dextran, wherein the hydroxyl groups on the dextran are oxidized to aldehyde groups to obtain the oxidized dextran which can further immobilize antibody.

Figure 1:
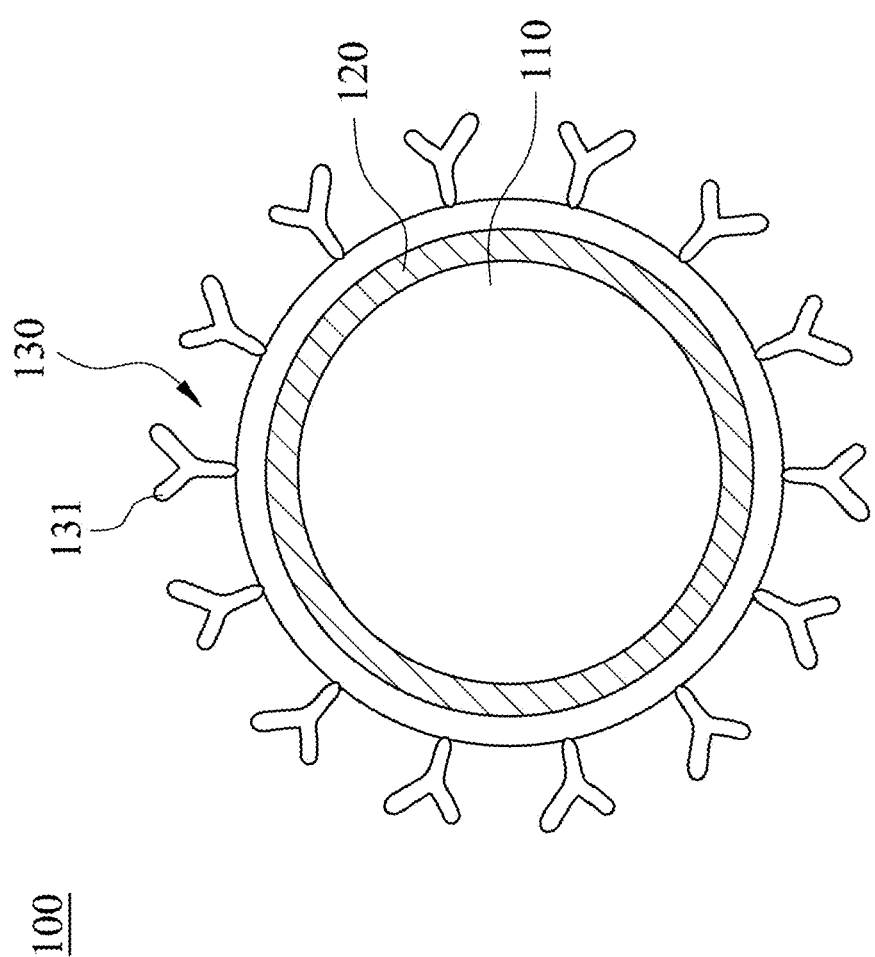
FIG. 1 is a structural schematic view showing an immunomagnetic nanocapsule according to the present disclosure.

Please refer to FIG. 1, which is a structural schematic view showing an immunomagnetic nanocapsule 100 according to the present disclosure. As shown in FIG. 1, the immunomagnetic nanocapsule 100 includes a core 110, a shell 120 and an outer layer 130.

The core 110 can includes an active substance. The active substance can be a cytokine or an anti-cancer drug.

The shell 120 is formed by a complex, wherein the complex is fabricated by a combination of the fucoidan, the oxidized dextran, and a plurality of superparamagnetic iron oxide nanoparticles via a hydrophobic interaction. The core 110 is encapsulated in the shell 120. Preferably, the fucoidan used to form the complex of the shell 120 can be extracted from *Undaria pinnatifida, Macrocystis pyrifera*, or *Fucus vesiculosus*. The oxidized dextran used can have an aldehyde group and can be prepared from a dextran with a molecular mass ranging from 5 kDa to 270 kDa. The hydrophobic interaction between the fucoidan, the oxidized dextran, and the superparamagnetic iron oxide nanoparticles can be caused by methods such as an emulsification or a nano-precipitation method. However, the present disclosure is not limited thereto.

The outer layer 130 includes at least one antibody 131 immobilized onto outside of the shell 120 to form the outer layer 130. The antibody 131 is an immune checkpoint inhibitor and/or a T cell expansion antibody. Preferably, the immune checkpoint inhibitor can be selected from the group consisting of a PD-L1 antibody, a PD-1 antibody, a CTLA-4 antibody and a TIM-3 antibody. The T cell expansion antibody is selected from the group consisting of a CD3 antibody, a CD28 antibody and a 4-1BB antibody.

Preferably, the immunomagnetic nanocapsule 100 can be a sphere with a particle size ranging from 80 nm to 350 nm. In addition, the immunomagnetic nanocapsule 100 can be a hollow shape.

Figure 2:
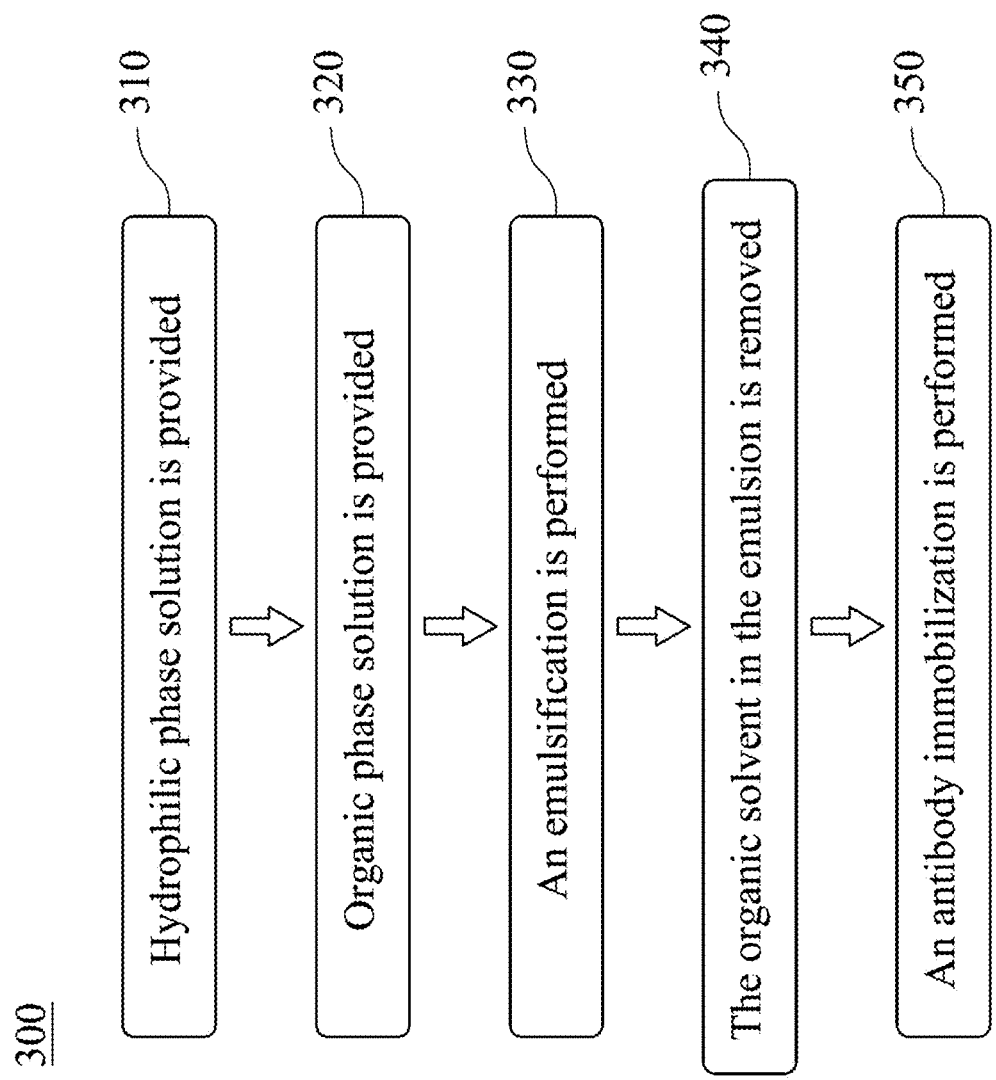
FIG. 2 is a flow chart showing a fabrication method of the immunomagnetic nanocapsule according to the present disclosure.

Please refer to FIG. 2, which is a flow chart showing a fabrication method of the immunomagnetic nanocapsule 300 according to the present disclosure. The fabrication method of the immunomagnetic nanocapsule 300 includes Step 310, Step 320, Step 330, Step 340 and Step 350.

In Step 310, a hydrophilic phase solution is provided. The hydrophilic phase solution includes the fucoidan and the oxidized dextran. The fucoidan can be extracted from *Undaria pinnatifida, Macrocystis pyrifera*, or *Fucus vesiculosus*. The oxidized dextran can be prepared from the dextran with the molecular mass ranging from 5 kDa to 270 kDa. The fucoidan and the oxidized dextran can be mixed in a weight ratio of 1:0.1 to 1:4.

In Step 320, an organic phase solution is provided. The organic phase solution includes an organic solvent and a plurality of superparamagnetic iron oxide nanoparticles. The organic solvent can be methane, dichloromethane or chloroform.

In Step 330, the emulsification is performed. The hydrophilic phase solution provided in step 310 and the organic phase solution provided in step 320 are mixed to form an emulsion.

In Step 340, the organic solvent in the emulsion can be removed by evaporation under reduced pressure to form a magnetic fucoidan nanoparticle.

In Step 350, an antibody immobilization is performed. At least one antibody is immobilized onto the magnetic fucoidan nanoparticle to form the immunomagnetic nanocapsule. The antibody used is the immune checkpoint inhibitor and/or the T cell expansion antibody. Preferably, the immune checkpoint inhibitor can be selected from the group consisting of the PD-L1 antibody, the PD-1 antibody, the CTLA-4 antibody and the TIM-3 antibody. The T cell expansion antibody can be selected from the group consisting of the CD3 antibody, the CD28 antibody and the 4-1BB antibody.

The immunomagnetic nanocapsule fabricated by the aforementioned fabrication method can be used as the pharmaceutical composition for treating cancer. The pharmaceutical composition for treating cancer includes the immunomagnetic nanocapsule and a pharmaceutically acceptable carrier. The pharmaceutical composition for treating cancer can be used for inhibiting a proliferation of cancer cells, reducing a metastasis of cancer cells and triggering a tumor immune response. The immunomagnetic nanocapsule fabricated by the aforementioned fabrication method is shown as the hollow shape, hence the active substance can be further encapsulated in the core of the immunomagnetic nanocapsule to enhance the anticancer effect of the pharmaceutical composition for treating cancer.

The immunomagnetic nanocapsule fabricated by the aforementioned fabrication method can be cooperated with a magnetic field generator as the kit for treating cancer. The magnetic field generator can be a device which can generate a magnetic field, such as a magnet, a three-dimensional field magnet or a magnetic resonance imaging scanner. The magnetic field generated by the magnetic field generator can be used as an auxiliary tool for a magnetic navigation, and the immunomagnetic nanocapsule of the present disclosure can be accumulated in the affected part to achieve the effect of local treatment. Therefore, the dose of the antibody in the kit for treating cancer of the present disclosure is only one percent of the dose of pure antibody administered in general, and the kit for treating cancer is able to exhibit more excellent tumor inhibiting ability and extend the half-life by more than 2 times.

The immunomagnetic nanocapsule, the pharmaceutical composition for treating cancer and the kit for treating cancer has been described as mentioned above. In the following, reference will now be made in detail to the present embodiments of the present disclosure, experiments and examples of which are illustrated in the accompanying drawings. The accompanied effects of the immunomagnetic nanocapsule, the pharmaceutical composition for treating cancer and the kit for treating cancer disclosed in the experiments and the examples for demonstrating the effect and the mechanism of the immunomagnetic nanocapsule, the pharmaceutical composition for treating cancer and the kit for treating cancer in the immunotherapy through a breast cancer metastasis mouse model and a colorectal cancer mouse model. However, the present disclosure is not limited thereto.

EXPERIMENTS AND EXAMPLES

I. The Immunomagnetic Nanocapsule of the Present Disclosure and the Fabrication Method Thereof 1.1 Structure and Stability Analysis of the Magnetic Fucoidan Nanoparticle To test the optimal preparation condition of the immunomagnetic nanocapsule, the magnetic fucoidan nanoparticle without immobilized antibody is fabricated in this experiment first. The structure of the magnetic fucoidan nanoparticle is analyzed by a scanning electron microscopy (SEM) and a transmission electron microscopy (TEM). The zeta potential (ZP) of the magnetic fucoidan nanoparticle, the particle size of the magnetic fucoidan nanoparticle and the stability of the magnetic fucoidan nanoparticle dispersed in distilled deionized water (DDW) and phosphate buffered saline (PBS) are analyzed by a particle analyzer (Delsa Nano C particle analyzer, BECKMAN COULTER).

Before fabricating the magnetic fucoidan nanoparticle, the superparamagnetic iron oxide nanoparticles and the oxidized dextran are prepared, respectively. The oxidized dextran used in this experiment has the aldehyde group for subsequent immobilizing the antibody. The superparamagnetic iron oxide nanoparticles (hereafter "IO") are modified and prepared by consulting the literature published by Shouheng Sun in 2004 (Shouheng Sun et al., Monodisperse $MFe_2O_4$ (M=Fe, Co, Mn) Nanoparticles. Journal of the American Chemical Society 2004, 126(1): 273-279). In brief, 2 mmol of $Fe(acac)_3$, 10 mmol of 1,2-hexadecanediol, 6 mmol of oleic acid, and 6 mmol of olecylamine are mixed in 20 ml of benzyl ether to refluxed at 100° C. for 30 minutes under nitrogen atmosphere. The mixture aforementioned is next sequentially heated to 200° C. for 1-hour, and to 285° C. for 30 minutes to complete the nucleation and growth of the superparamagnetic iron oxide nanoparticles. After cooling to room temperature, the superparamagnetic iron oxide nanoparticles are collected by centrifugation at 6,000 rpm for 10 minutes, and purified with ethanol for 3 times.

The oxidized dextran with the aldehyde group (hereafter "Dex") is prepared as follows. The dextran (the molecular mass ranges from 5 kDa to 270 kDa) is dissolved in an aqueous oxidation buffer (0.5-10 mg ml-1, pH=5.5) containing sodium periodate solution (10 mM) for 30 minutes at room temperature in dark for oxidation. To remove the sodium meta-periodate, the Dex is dialyzed using Amicon (Mw=3 kDa), re-dispersed, and lyophilized using Lyophilizer (FreeZone 1L Benchtop Freeze Dry Systems, Labconco, Kans.). The structure of the Dex is characterized using a nuclear magnetic resonance (NMR), and the degree of modification of the Dex is characterized using a colorimetric aldehyde assay kit (MAK140, sigma).

In this experiment, the magnetic fucoidan nanoparticle is fabricated as follows. 0.5 mg/ml of the fucoidan (extracted from *Fucus vesiculosus*) and 0.5 mg/ml of the Dex are mixed as the hydrophilic phase solution. 2 mg of the IO is dissolved in 0.2 ml of the dichloromethane as the organic phase solution. The hydrophilic phase solution and the organic phase solution are mixed and then emulsified (120 W) for 50 seconds using a homogenizer (Double Eagle Enterprise Co, Ltd) to obtain an emulsion. After the dichloromethane is removed using rotary evaporator, the magnetic fucoidan nanoparticles (hereafter "IO@FuDex") are purified by using the magnetic selection equipment (MagniSort®, eBioscience). After depleting the excess materials, the IO@FuDex are re-suspended with DDW or 0.1 M PBS (pH=6) for further surface modification. In addition, magnetic nanoparticles IO@Fu are fabricated using the same fabrication method except the hydrophilic phase solution is 0.5 mg/ml of the fucoidan. Magnetic nanoparticles IO@Dex are also fabricated using the same fabrication method except the hydrophilic phase solution is 0.5 mg/ml of the Dex. The structures of the IO@FuDex, the IO@Fu and the IO@Dex are analyzed by the SEM and the TEM. The ZP and the particle size of the IO@FuDex, the IO@Fu and the IO@Dex are analyzed by the particle analyzer. The magnetic analysis of the IO@FuDex is analyzed by a superconducting quantum interference magnetometer (SQUID).

Figure 3A:
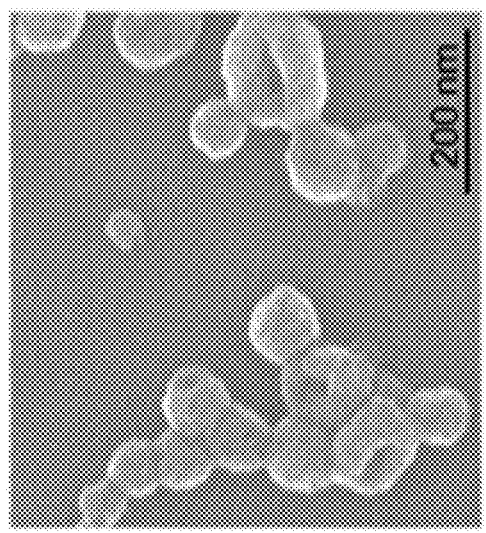
FIGS. 3A, 3B, 3C, 3D, 3E and 3F show structural analysis results of a magnetic fucoidan nanoparticle.
Figure 6A:
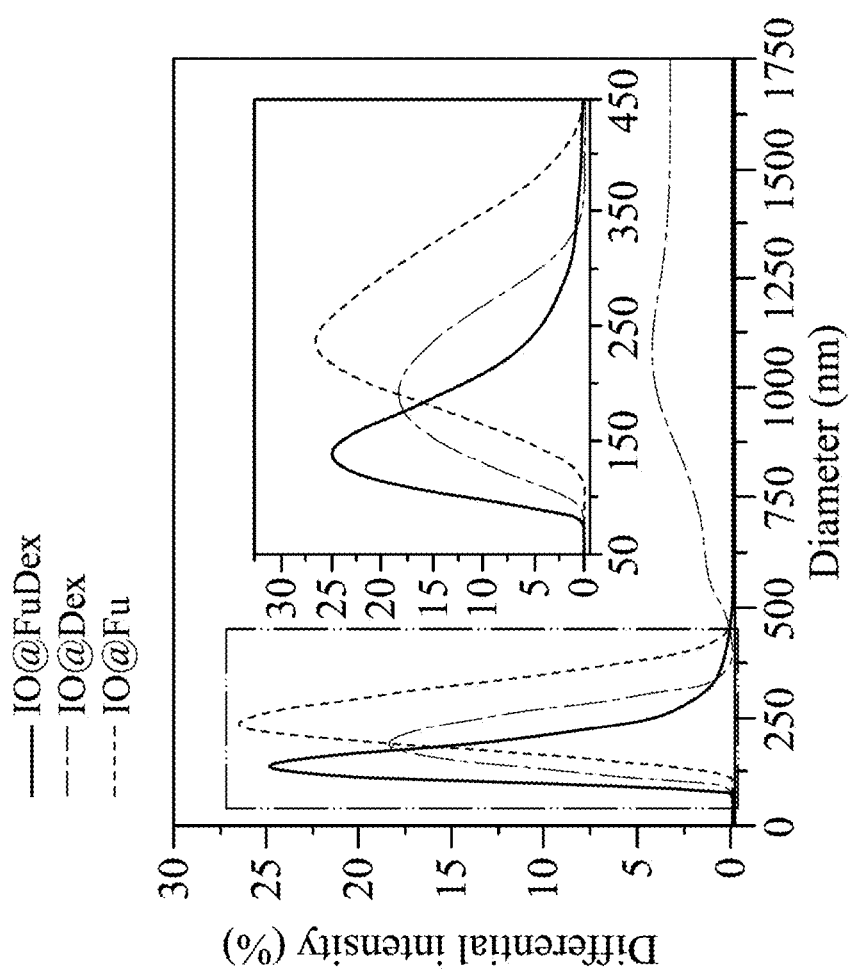
FIGS. 6A, 6B and 6C show stability analysis results of the magnetic fucoidan nanoparticle.
Figures 6B, 6C:
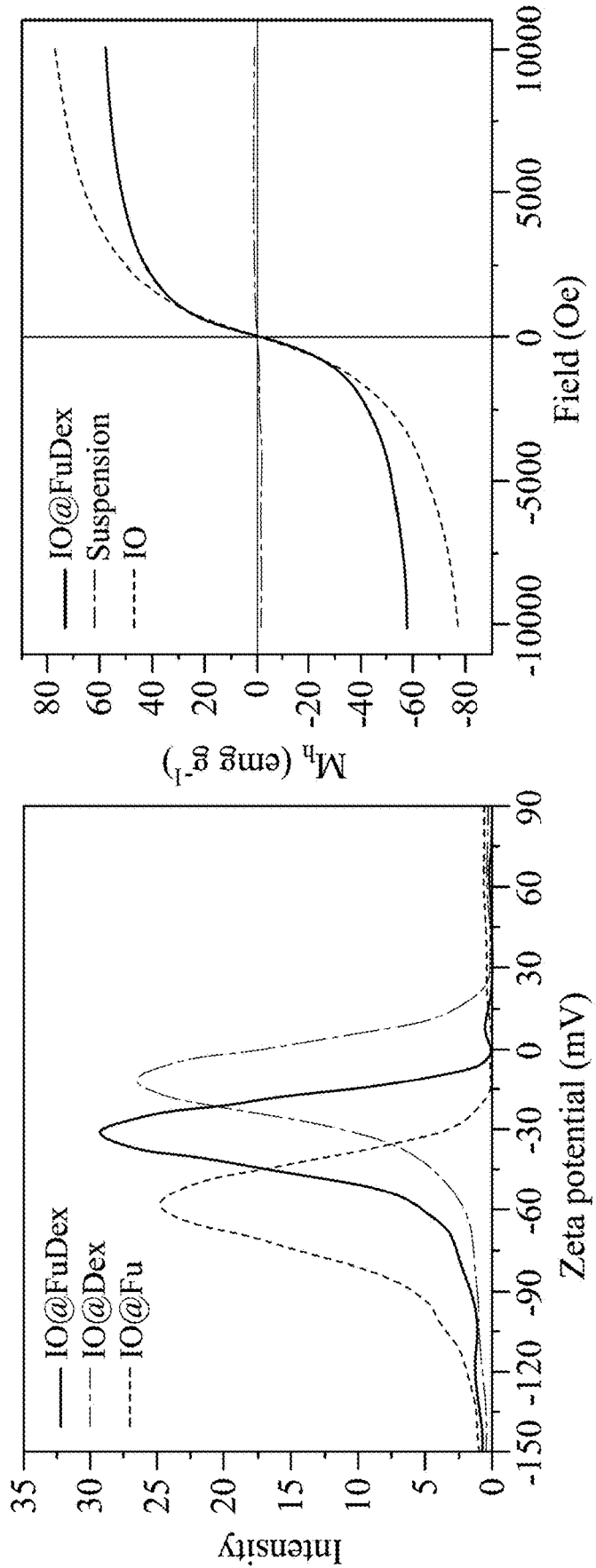

Please refer to FIGS. 3A to 6C. FIGS. 3A to 3F show structural analysis results of the IO@FuDex, wherein the FIG. 3A is a scanning electron micrograph of the IO@FuDex, and FIGS. 3B to 3F are transmission electron micrographs of the IO@FuDex. FIGS. 4A to 4C show structural analysis results of the IO@Fu, wherein FIGS. 4A and 4B are scanning electron micrographs of the IO@Fu, and FIG. 4C is a transmission electron micrograph of the IO@Fu. FIGS. 5A and 5B show structural analysis results of the IO@Dex, wherein FIG. 5A is a scanning electron micrograph of the IO@Dex, and FIG. 5B is a transmission electron micrograph of the IO@Dex. FIGS. 6A to 6C show stability analysis results of the IO@FuDex, wherein FIG. 6A shows hydrodynamic size distribution of the IO@FuDex, the IO@Fu and the IO@Dex, FIG. 6B shows ZP analysis result of the IO@FuDex, the IO@Fu and the IO@Dex, and FIG. 6C shows magnetization analysis result of the IO@FuDex and IO.

Figure 3B:
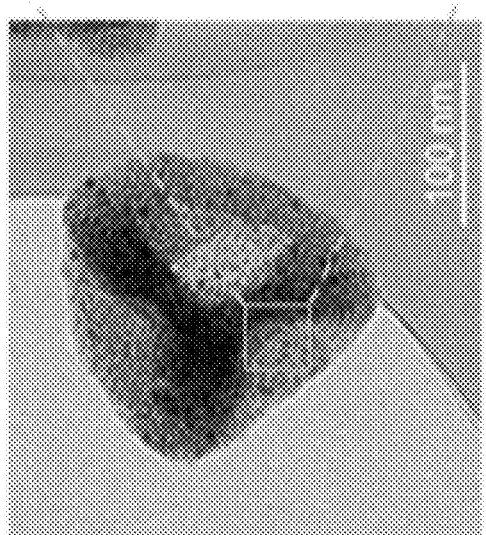
Figure 3C:
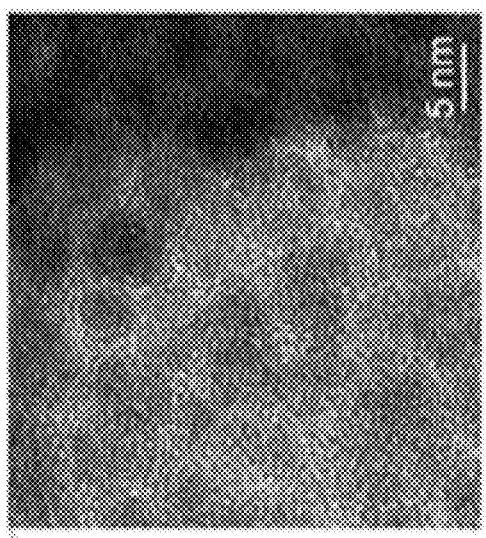
Figure 3D:
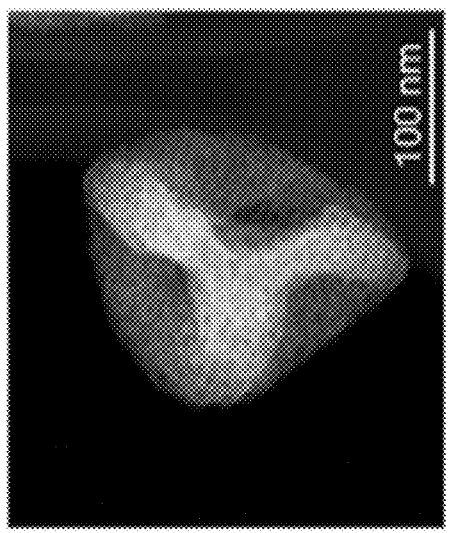
Figure 3E:
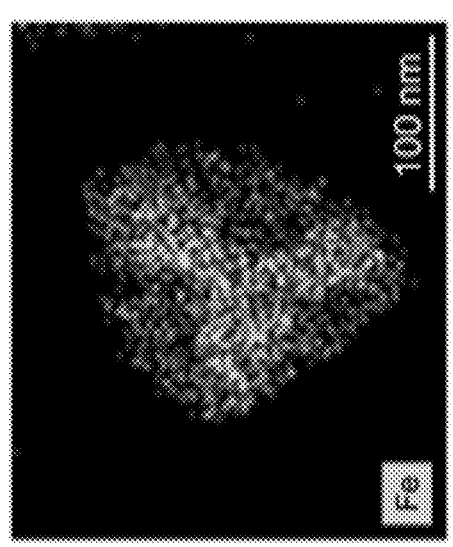
Figure 3F:
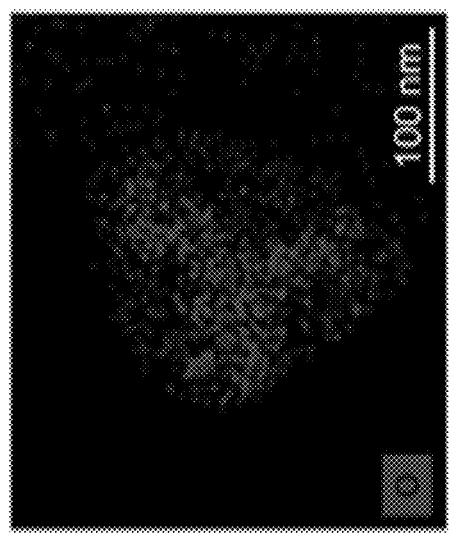
Figure 4A:
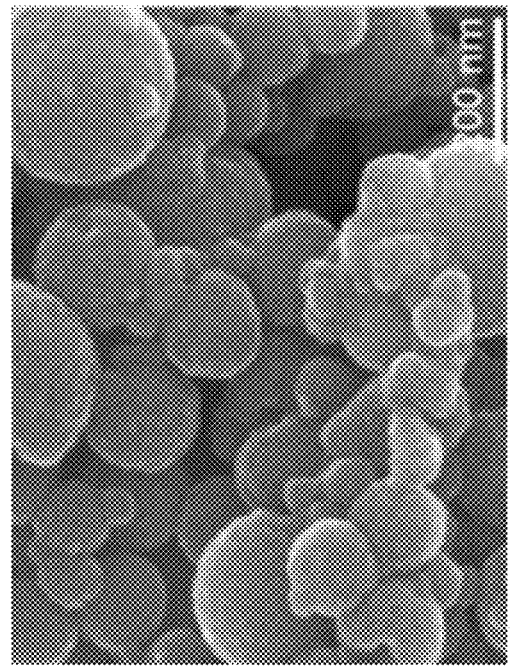
FIGS. 4A, 4B and 4C show structural analysis results of a magnetic nanoparticle IO@Fu.
Figure 4B:
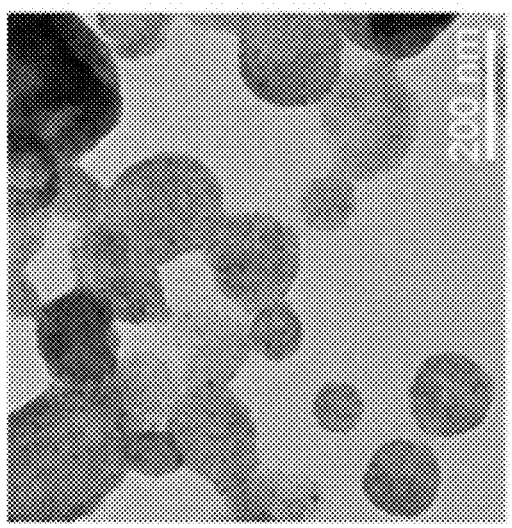
Figure 4C:
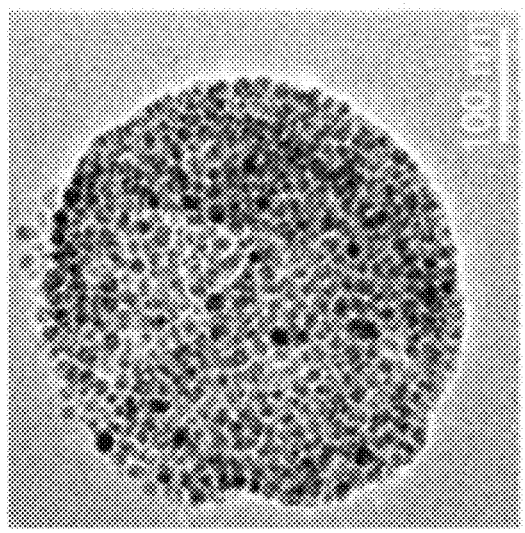
Figures 5A, 5B:
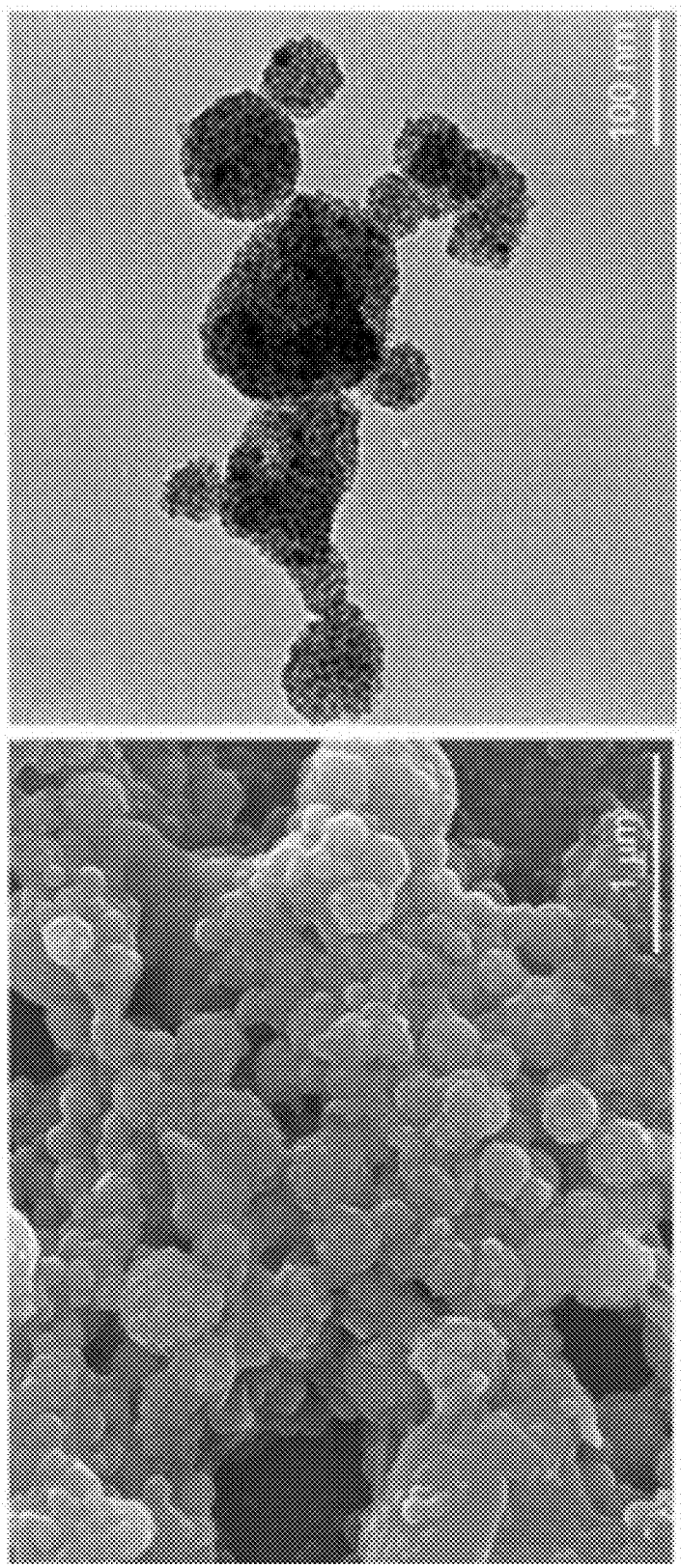
FIGS. 5A and 5B show structural analysis results of a magnetic nanoparticle IO@Dex.

In FIG. 3A, the IO@FuDex is the sphere and collapsed under high-vacuumed condition under SEM analysis, which represents that the IO@FuDex is a hollow structure. In FIG. 3B, the dark contrast caused by the overlaying shells can be observed under TEM analysis. FIG. 3C is a transmission electron micrograph at a partial enlarged view of the shell. In FIG. 3C, many superparamagnetic iron oxide nanoparticles with the size of about 5 nm can also be observed, which proves that the superparamagnetic iron oxide nanoparticle is the structure of the shell. Under the dark field observation in FIG. 3D and the elemental distribution detection in FIGS. 3E and 3F, the hollow structure and the distribution of iron oxide in the IO@FuDex can be obvious observed again.

In FIGS. 4A to 5B, the IO@Fu exhibits homogeneous structure as the IO@FuDex, while the IO@Dex is not stable. The IO@Dex tends to aggregate during the evaporation process, resulting in a wide distribution of particle size and random morphological appearance.

In FIGS. 6A and 6B, the IO@FuDex is monodispersed in the fluid with the particle size ranging from 80 nm to 350 nm. An average particle size of the IO@FuDex is 141.5 nm, which is smaller than the average particle size of IO@Fu (241 nm). Both the IO@Fu and the IO@FuDex, mainly stabilized by the fucoidan, exhibit strong negative ZP due to the sulfate in the fucoidan, with IO@FuDex co-stabilized by the Dex having lower ZP (−32.8 mV) than the IO@Fu (−58.4 mV). Therefore, the strong repellent force between the IO@FuDexs can keep the colloid stable and well-dispersed. In FIG. 6C, the IO has a very high saturation magnetization per unit weight. The saturation magnetization value of the IO@FuDex is slightly lower due to its inclusion of the IO, the fucoidan and the Dex, but the IO@FuDex still possesses strong magnetic properties with 57.5 emu g$^{-1}$ of magnetization. The result indicates that strength of the magnetization of the IO@FuDex does not decrease due to the formation of a composite structure, which facilitates the magnetic purification using a magnetic separation equipment for obtaining high yields of the IO@FuDex.

The IO@FuDex is further fabricated by the Dex with different molecular mass. The IO@FuDex is fabricated by the aforementioned fabrication method, but the Dex in the hydrophilic phase solution provided in Step 310 of FIG. 2 is prepared from the dextran with the molecular mass ranging from 5 kDa to 270 kDa, respectively. Then the Dex and the fucoidan are mixed in the weight ratio of 1:0.2. Details of the remaining Steps 320 to 340 are substantially the same as described in Experiment 1.1, and the details are not described herein again. Then the particle size of the IO@FuDex are analyzed by the particle analyzer, the results are shown in the following Table 1:

TABLE 1

The average particle size of the IO@FuDex fabricated by different molecular mass of the Dex

| Molecular mass of dextran (kDa) | average particle size (nm) |
|---|---|
| 5 | 132 ± 14.5 |
| 12 | 130 ± 9.8 |
| 25 | 141 ± 16.2 |
| 50 | 162 ± 23.6 |
| 80 | 176 ± 26.8 |
| 150 | 203 ± 48.6 |
| 270 | 264 ± 32.6 |

The IO@FuDex is further fabricated by different weight ratio of the fucoidan and the Dex. The IO@FuDex is fabricated by the aforementioned fabrication method, but the fucoidan and the Dex in the hydrophilic phase solution provided in Step 310 of FIG. 2 is mixed in the weight ratio of 1:0.1 to 1:4, respectively. Then the Dex and the fucoidan are mixed in the weight ratio of 1:0.2. Details of the remaining Steps 320 to 340 are substantially the same as described in Experiment 1.1, and the details are not described herein again. Then the particle size of the IO@FuDex are analyzed by the particle analyzer, the results are shown in the following Table 2:

TABLE 2

The average particle size of the IO@FuDex fabricated by different weight ratio of the fucoidan and the Dex

| the fucoidan:the Dex (weight ratio) | average particle size (nm) |
|---|---|
| 1:0.1 | 145 ± 6.9 |
| 1:0.2 | 153 ± 11.6 |
| 1:1 | 130 ± 9.8 |
| 1:2 | 141 ± 16.2 |
| 1:3 | 162 ± 23.6 |
| 1:4 | 176 ± 26.8 |

To test whether the IO@FuDex lyophilized and then re-dispersed in an aqueous solution remains the same structure, the fabricated IO@FuDex is further lyophilized by the lyophilizer to form a powdery crystal in this experiment. The lyophilized powdery crystal is re-dispersed in an aqueous solution, and the structure of the IO@FuDex before and after lyophilized are observed under the TEM analysis.

Please refer to FIGS. 7A and 7B. FIG. 7A is a transmission electron micrograph of the IO@FuDex before lyophilized. FIG. 7B is a transmission electron micrograph of the IO@FuDex after lyophilized. In FIG. 7A, the structure of the IO@FuDex before lyophilized is a hollow sphere with the particle size ranging from 80 nm to 350 nm. The lyophilized powdery crystal can be rapidly re-dispersed in the aqueous solution. In FIG. 7B, the structure of IO@FuDex re-dispersed remains as the hollow sphere with the particle size consistent with the IO@FuDex before lyophilized under the TEM analysis. These results indicate that the stability of the IO@FuDex is excellent.

1.2 Synthesis of Examples 1-3

The immunomagnetic nanocapsule of the present disclosure is further fabricated under the optimal condition described above for fabricating the IO@FuDex. The fabricated IO@FuDexs are incubated with different antibodies in the buffer (0.1 M, pH=6) containing 5 M sodium cyanoborohydride performing antibody immobilization for 4-6 hours at 4° C. A dynamic process of the immobilization starts as the aldehydes in the Dex form Schiff bases with the primary amines on antibodies, and the immobilization further becomes chemically stabilized after undergoing reductive amination reaction with the use of sodium cyanoborohydride. The fabricated immunomagnetic nanocapsules are purified using the magnetic separation equipment. Please refer to following Table 3, which represents the antibodies used in examples 1-3. The antibodies used in the example 1 are the CD3 antibody and the CD28 antibody, the antibody used in the example 2 is the PD-L1 antibody, and the antibodies used in the example 3 are the PD-L1 antibody, the CD3 antibody and the CD28 antibody.

TABLE 3

|  | PD-L1 antibody | CD3 antibody | CD28 antibody |
|---|---|---|---|
| IO@FuDex | − | − | − |
| example 1 | − | + | + |
| example 2 | + | − | − |
| example 3 | + | + | + |

The fabricated examples are analyzed for the structure and elemental analysis by the TEM and for elemental composition in the example 3 by X-ray photoelectron spectroscopy (XPS).

Figure 8:
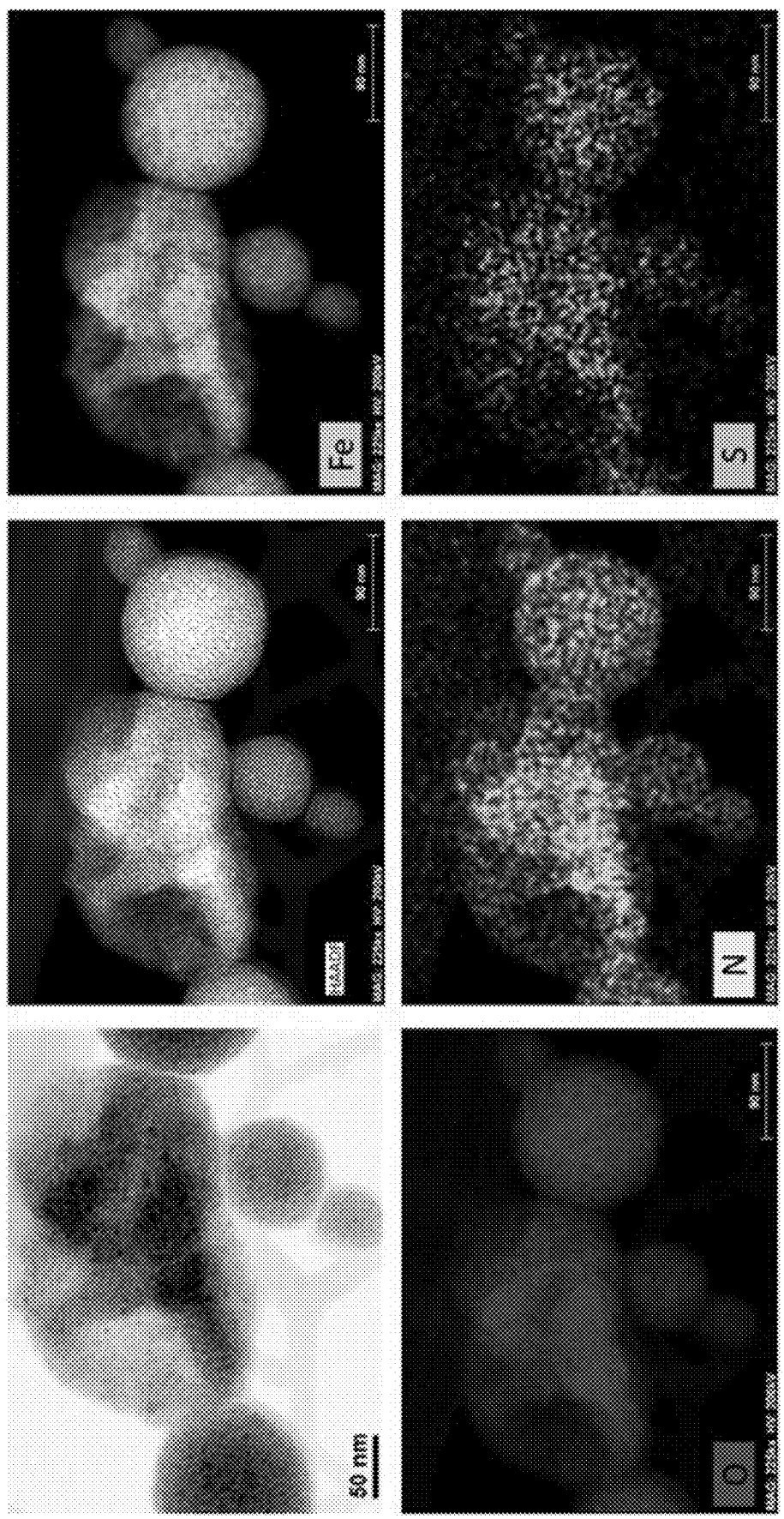
FIG. 8 shows structural analysis results of an immunomagnetic nanocapsule according to one example of the present disclosure.

Please refer to FIG. 8, which shows structural analysis results of the example 3. In FIG. 8, the structure of the example 3 is a spherical hollow structure with the particle size of about 80 nm to 350 nm. The elemental analysis of the electron microscopy revealed that the outer layer of the example 3 shows a uniform nitrogen signal (N) because of the presence of the antibody. Before immobilizing the antibody, the composition of the IO@FuDex is only sugars and iron oxide, and there is no material with nitrogen. After immobilizing the antibody, the antibody has many amino and peptide bonds with a large amount of nitrogen. The result indicates that the immunomagnetic nanocapsule of the present disclosure includes the antibody.

Figure 9:
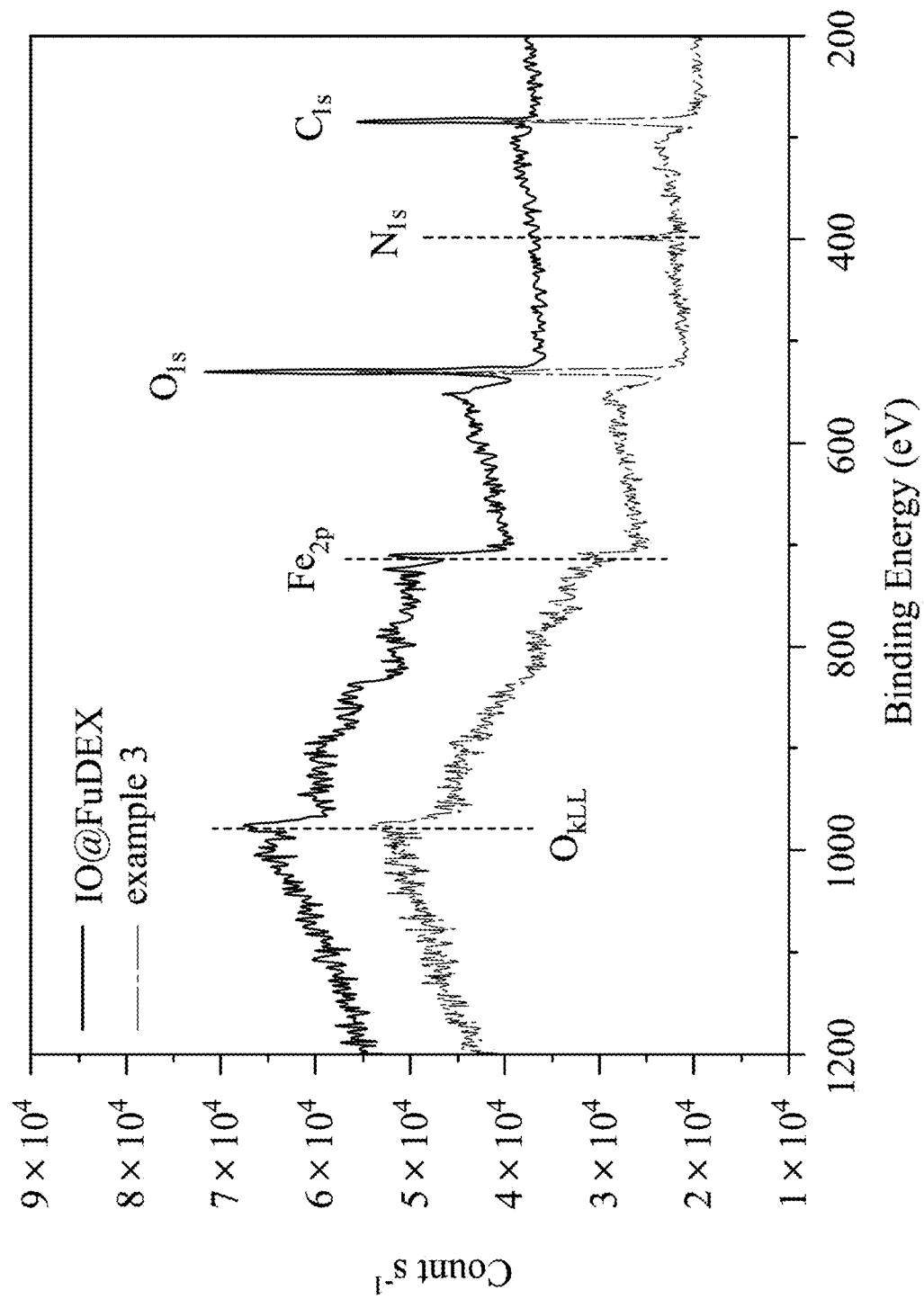
FIG. 9 shows X-ray photoelectron spectroscopy analysis results of the immunomagnetic nanocapsule according to one example of the present disclosure.

Please refer to FIG. 9, which shows XPS analysis results of the example 3. Compared with the IO@FuDex, the example 3 has an added signal with a bonding energy at 399 eV, which is a nitrogen signal. The result indicates that the antibody is successfully immobilized onto the example 3.

1.3 Synthesis and Structure Confirmation of Example 5

The immunomagnetic nanocapsule is shown as the hollow shape, hence the active substance, such as the cytokine or the anti-cancer drug can be encapsulated in the core of the immunomagnetic nanocapsule. The active substance used in this experiment is Interleukin-2 (IL-2) for preparing the example 5 including the IL-2.

In this experiment, the example 5 is fabricated as follows. 0.5 mg/ml of the fucoidan, 0.5 mg/ml of the Dex and 50 μg are mixed as the hydrophilic phase solution. 2 mg of the IO is dissolved in 0.2 ml of the dichloromethane as the organic phase solution. The hydrophilic phase solution and the organic phase solution are mixed and then emulsified (120 W) for 50 seconds using a homogenizer to obtain the emulsion. After the dichloromethane is removed using rotary evaporator, the example 5 is purified by using the magnetic selection equipment. The structure of the fabricated example 5 is analyzed by the SEM. The particle size of the fabricated example 5 is analyzed by the particle analyzer.

Figure 10B:
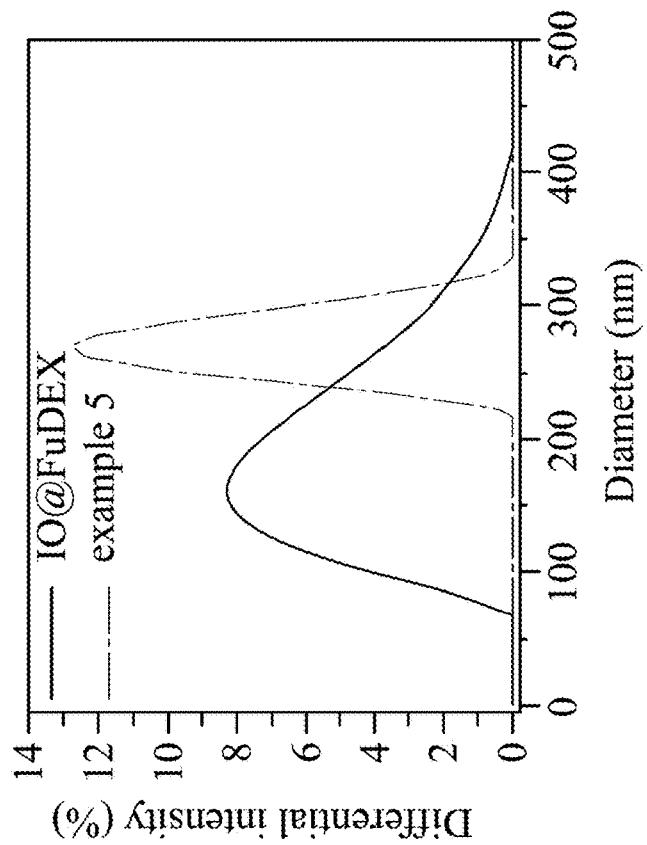
FIGS. 10A and 10B show structural analysis results of an immunomagnetic nanocapsule according to another example of the present disclosure.
Figure 10A:
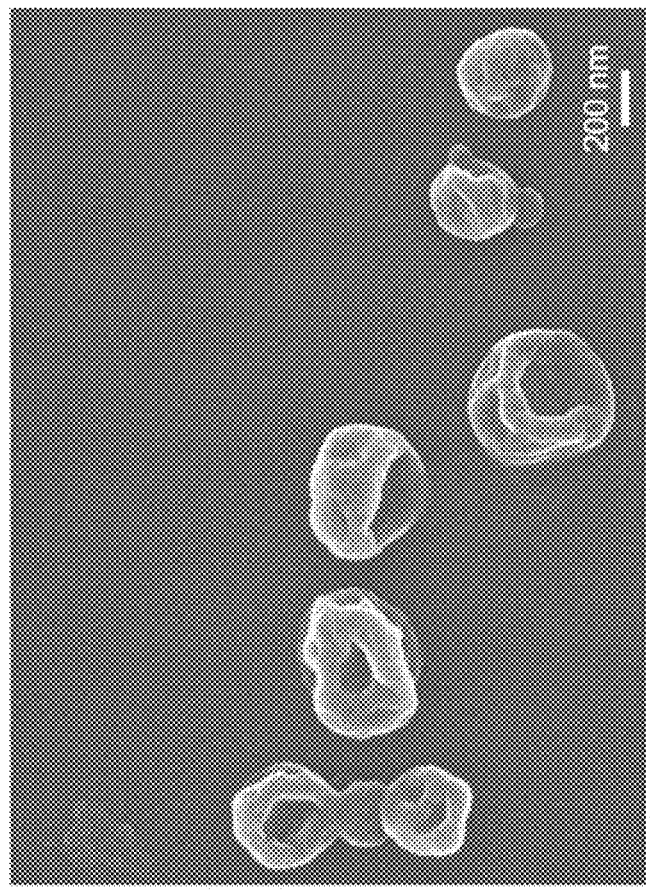

Please refer to FIGS. 10A and 10B, which are structural analysis results of example 5. FIG. 10A is a scanning electron micrograph of the example 5, and FIG. 10B shows hydrodynamic size distribution of the example 5. The entrapment efficiency of the IL-2 in the example 5 is 99.93%. Because the IL-2 fills the core, compared with the average particle size of the IO@FuDex (161.2 nm), the average particle size of the example 5 is increased to 356.2 nm. The result indicates that the active substance can be further encapsulated in the core of the immunomagnetic nanocapsule of the present disclosure. Other active substances, such as Doxorubicin, Docetaxel, Paclitaxel or Astaxanthin (ASTX), also can be encapsulated in the immunomagnetic nanocapsule of the present disclosure using the same fabrication method.

1.4 Targeting Ability Analysis of the Immunomagnetic Nanocapsule of the Present Disclosure In this experiment, the fabricated examples 1-3 are performed the targeting ability analysis and the cell association ability analysis to examine whether the immunomagnetic nanocapsule of the present disclosure can reverse the decline of T-cell immunity and enhance tumor regression in mice. The aggressive and triple negative breast cancer cell line (4T1) with metastatic capacity and PD-L1 expression is selected as the experimental model. To achieve the observation of examples 1-3 under fluorescence microscopy analysis, quantum-dot (QD) is further incorporated into the structure of the examples 1-3 of fluorescence microscopy analysis group, respectively.

To assess targeting behavior in vitro, the examples 1-3 are incubated with the 4T1-Luc cells ($4 \times 10^5$) in the presence of 2 wt % bovine serum albumin (BSA) under 4° C. for 30 minutes, and analyzed using flow cytometry (Novocyte Flow Cytometer, ACEA Biosciences). To access the cell association behavior, IO@FuDex incorporated with the QD and the example 2 incorporated with the QD are incubated with the 4T1-Luc cells for 1, 4, 12 and 24 hours, and either analyzed using flow cytometry or fluorescent microscopy (Carl Zeiss, Thornwood, N.Y., USA).

Figures 11A, 11B:
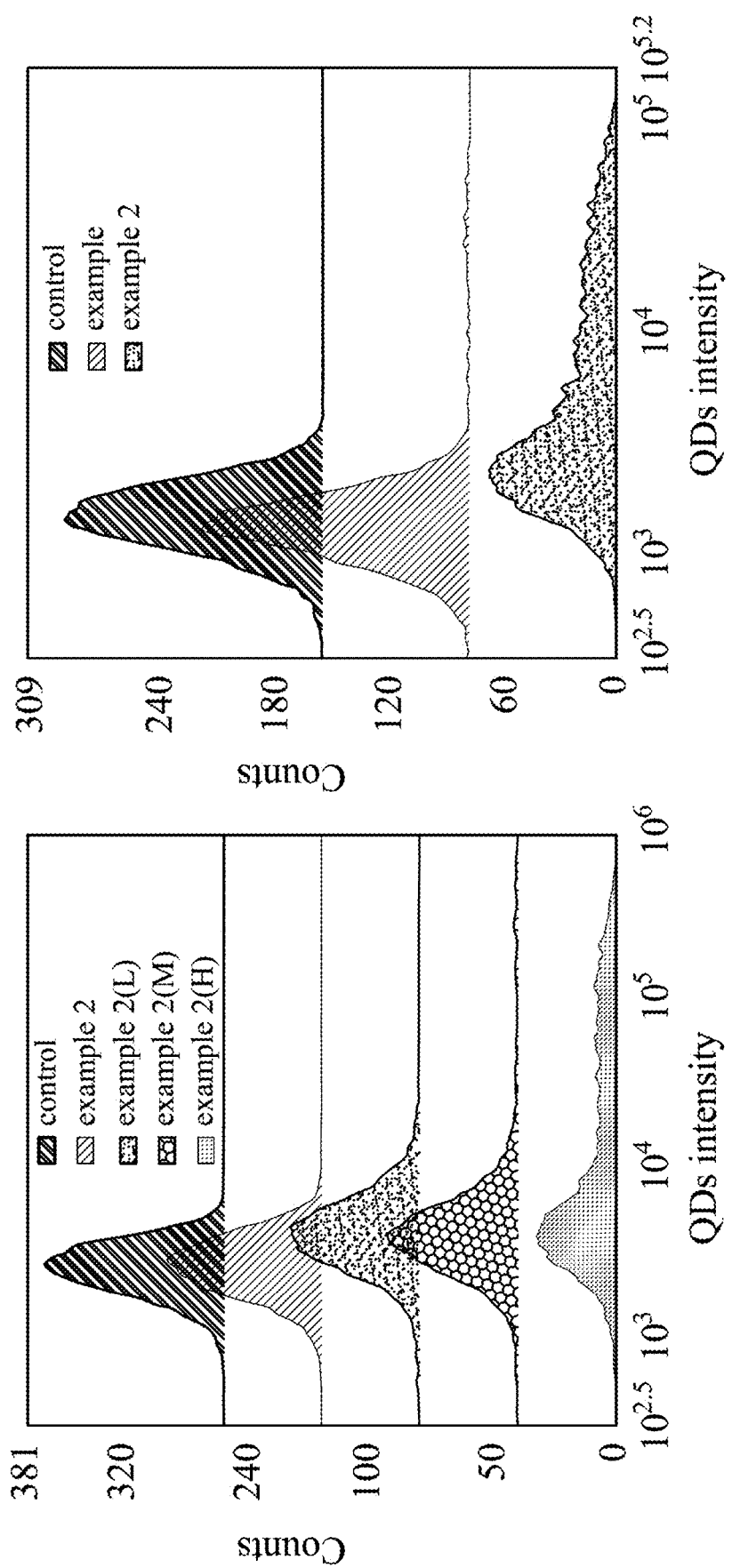
FIGS. 11A, 11B, 11C, 11D, 11E and 11F show targeting ability analysis and cell association ability analysis results of the immunomagnetic nanocapsule of the present disclosure.
Figures 11C, 11D:
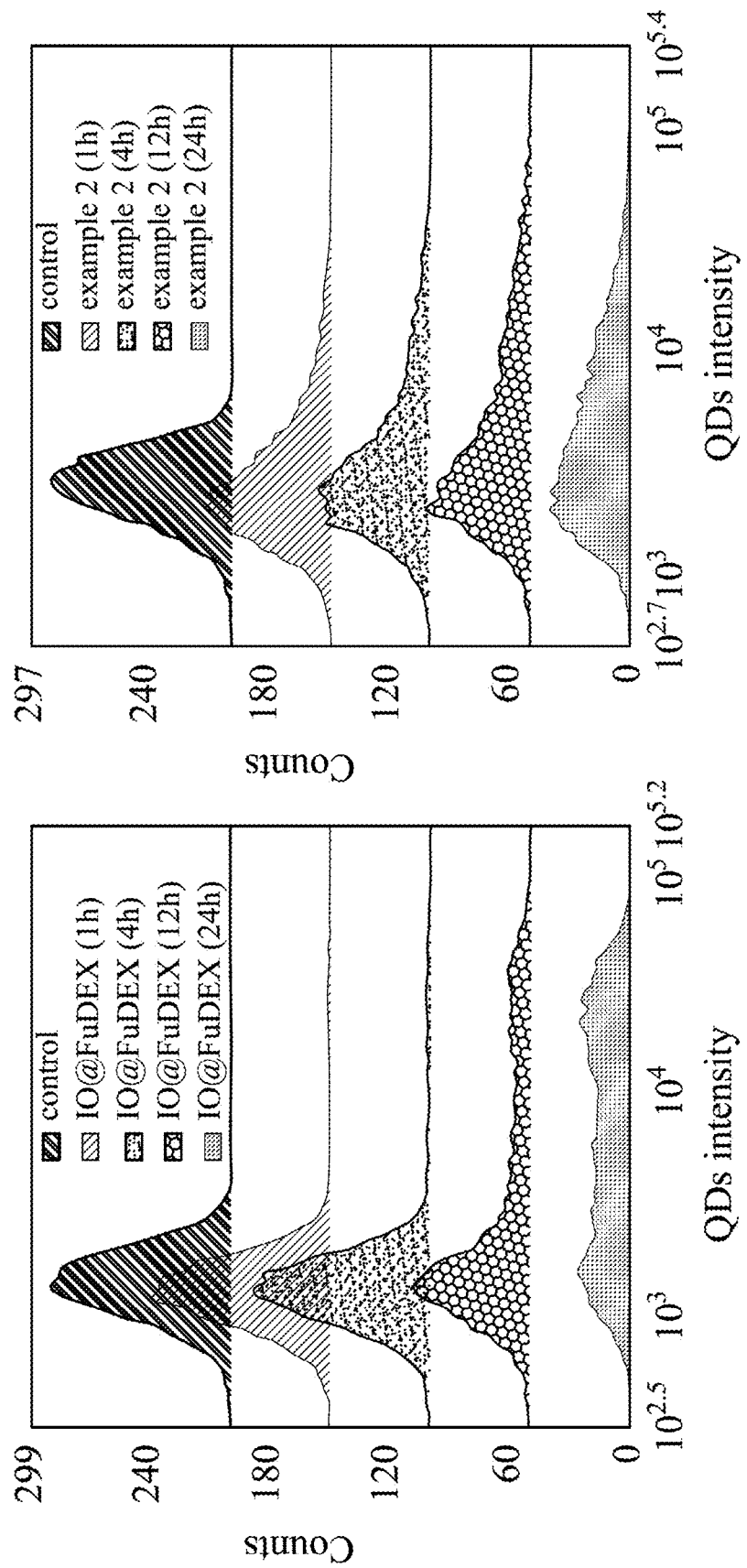
Figures 11E, 11F:
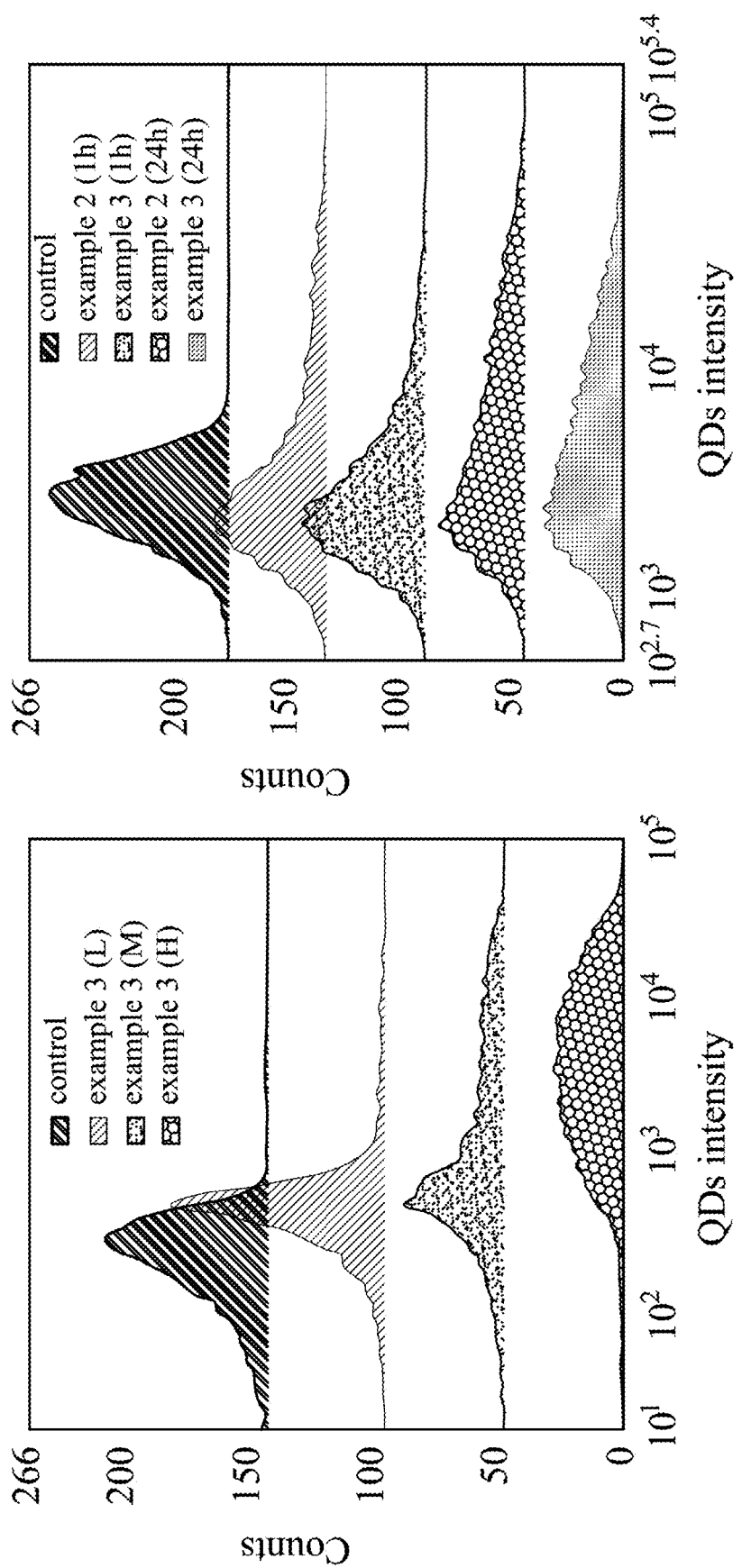

Please refer to FIGS. 11A to 11F, which show targeting ability and cell association ability analysis results of the immunomagnetic nanocapsule of the present disclosure. FIG. 11A shows the targeting ability analysis results of the example 2 with the PD-L1 antibody conjugation concentration of 1.4 μg/ml (low concentration, L), 7 μg/ml (medium concentration, M) and 35 μg/ml (medium concentration, M), respectively. FIG. 11B shows the targeting ability analysis results of the example 2 and an IgG-labeled IO@FuDex. FIG. 11C shows the 4T1 cell association ability analysis results of the IO@FuDex under 1, 4, 12 and 24 hours incubation. FIG. 11D shows the 4T1 cell association ability analysis results of the example 2 under 1, 4, 12 and 24 hours incubation. FIG. 11E shows the targeting ability analysis results of the example 3 with the CD3 antibody/CD28 antibody conjugation concentration of 1.4 μg/ml (low concentration, L), 7 μg/ml (medium concentration, M) and 35 μg/ml (medium concentration, M), respectively. FIG. 11F shows the 4T1 cell association ability analysis results of the example 2 and example 3 under 1 hour and 24 hours incubation.

In FIG. 11A, after 1-hour incubation at 4° C., 4T1 cells associate with the example 2 (H) exhibits the highest median fluorescence index (MDI). It indicates that the amount of the example 2 labeled onto PD-L1-expressed 4T1 cells is strongly correlated with the surface antibody density. Thus, the the example 2 (H) is selected for further experiments. In FIG. 11B, no MDI shift is observed for the IgG-labeled IO@FuDex, demonstrating the affinity to 4T1 cells is derived from the PD-L1 antibody instead of any non-specific interaction of IO@FuDex.

In FIGS. 11C and 11D, the amount of cell association is time-dependent for the IO@FuDex, which shows obvious cell uptake after 12 hours incubation. In contrast, the example 1 achieves cell association within 1-hour incubation, follows by a slow shift in MDI, which indicates more cell association of the example 2 as the incubation time increased. The result indicates that the immobilization of the PD-L1 antibody changes 4T1 cell association ability of the IO@FuDex.

Subsequently, to achieve the goal that the present disclosure can simultaneously be the immune checkpoint inhibitor and the T cell expansion agent, the example 3 is the immunomagnetic nanocapsule immobilizing the CD3 antibody, CD28 antibody and the PD-L1 antibody. FIG. 11E shows the targeting ability analysis results of the example 3 with different CD3 antibody/CD28 antibody conjugation concentration. In FIG. 11E, after 1-hour incubation at 4° C., 4T1 cells associate with the example 3 (H) exhibits the highest MDI, indicating strong affinity of the example 3 (H) to CD8$^+$ T cell. In FIG. 11F, the example 2 has similar 4T1 cell association behavior to the example 2, indicating that the immobilization of multiple antibodies does not impair the affinity of the immunomagnetic nanocapsule to 4T1 cells.

Please refer to FIGS. 12A to 12D, which show cell association ability analysis results of the example 3 binding to CD8$^+$ T cell. In this experiment, the CD8$^+$ T cells are incubated with the example 3 incorporated with the QD for 30 minutes, and then the CD8$^+$ T cells are fixed, stained using Alexa Fluor 488 Phalloidin and DAPI, and observed using confocal for confirming the position of the example related to the CD8$^+$ T cells. FIG. 12A represents the position of the nucleus, FIG. 12B represents the position of the example 3, FIG. 12C is a micrograph in the light field, and FIG. 12D is a merged micrograph, where the scale represents the length of 5 μm. In FIGS. 12A to 12D, a plurality of the example 3 can be observed in the CD8$^+$ T cells, indicating that the example 3 can bind to the CD8$^+$ T cells.

II. Therapeutic Effect of the Pharmaceutical Composition for Treating Cancer of the Present Disclosure 2.1 Therapeutic Effect of the Pharmaceutical Composition for Treating Cancer of the Present Disclosure on Treatment of Cancer The experiments in this part further demonstrate whether the pharmaceutical composition for treating cancer of the present disclosure has the therapeutic effect on cancer and whether it can be accumulated in the tumor via magnetic navigation (MN) in the breast cancer metastasis mouse model and the colorectal cancer mouse model.

2.1.1 Therapeutic Effect of the Pharmaceutical Composition for Treating Cancer of the Present Disclosure on Treatment of Lung Metastasis of Breast Cancer Six to eight-week-old female BALB/c (National Animal Center of Taiwan) mice are utilized for building the breast cancer metastasis mouse model using the 4T1-Luc cells. In brief, 4T1-Luc cells (1×10$^5$) are implanted in the 4th mouse mammary fat pad of female BALB/c mice at the right side of the abdomen. The 4T1-Luc tumor-bearing mice with a luciferase gene that stably express a biological luminescent enzyme (provided by the Center for Molecular Medicine, University Hospital of China Medical University) are used as the animal model in this experiment. The pharmaceutical composition for treating cancer including the I$^{125}$-labeled example 1, the I$^{125}$-labeled example 2 or the I$^{125}$-labeled example 3 is administered via the right femoral vein to the 4T1-Luc tumor-bearing mice, respectively. In addition, the example 4, which includes the I$^{125}$-labeled example 3 and a superficial round-shape magnet (diameter=0.5 cm, 0.5 Tesla) for the magnetic navigation, is included in this experiment as the kit for treating cancer. The dynamic intratumoral accumulation of the I$^{125}$-labeled example 3 and the example 4 are monitored using single-photon emission computed tomography (SPECT).

Figure 13C:
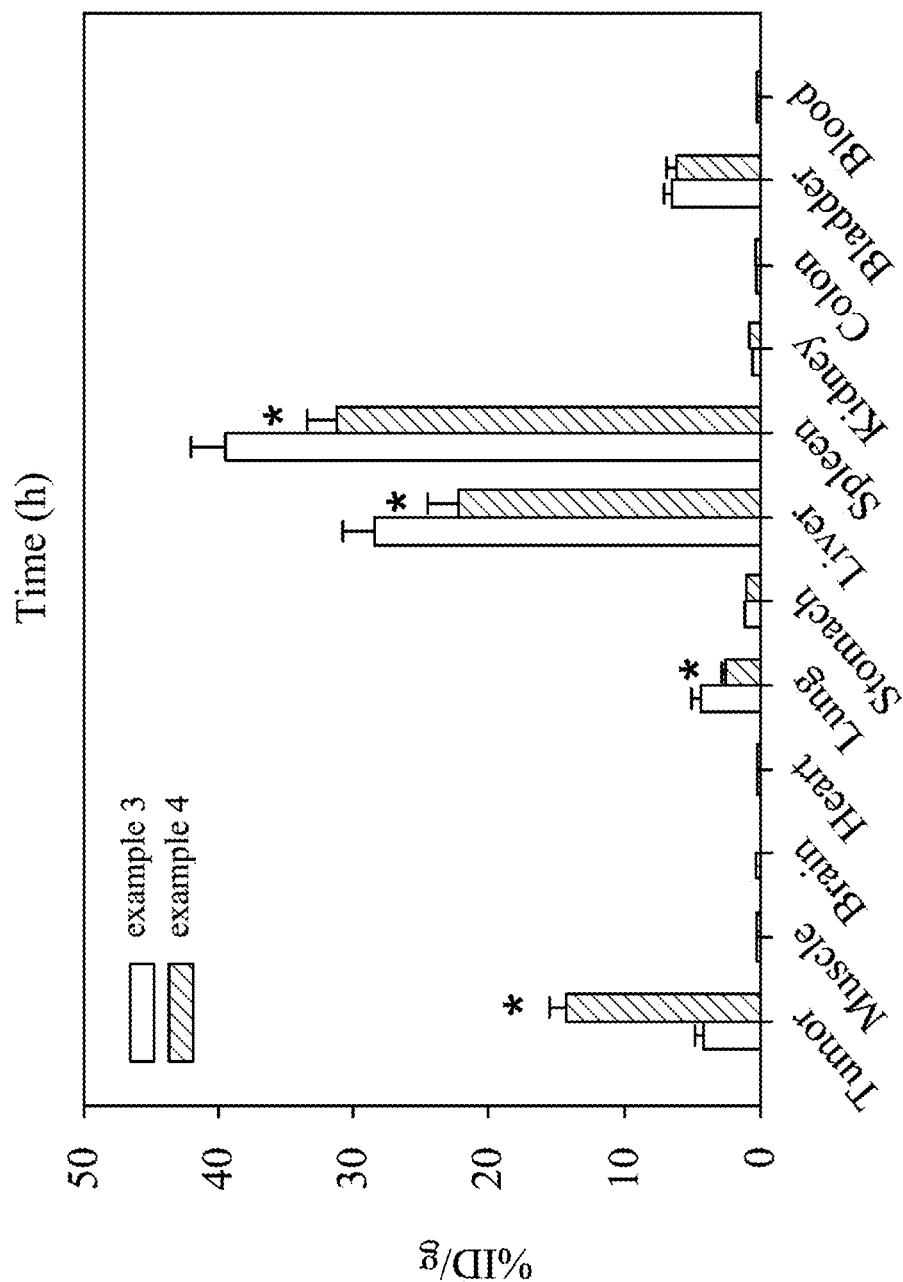

Please refer to FIGS. 13A to 13C, which show analysis results of nanomedicine accumulation in tumor of the kit for treating cancer of the present disclosure. FIG. 13A shows time-activity curves of the I$^{125}$-labeled example 3 or the example 4 in the 4T1-Luc tumor-bearing mice at the time points of 0, 4, 6, 12, and 24 hours, wherein n=4. FIG. 13B shows whole-body single photon emission computed tomography (SPECT) images of the 4T1-Luc tumor-bearing mice at 24 hours after administering the I$^{125}$-labeled example 3 or the example 4. FIG. 13C shows biodistribution quantitative profiles of the 4T1-Luc tumor-bearing mice at 24 hours after intravenous infusion of the I$^{125}$-labeled example 3 or the example 4, wherein n=4, and marked asterisks (*) represents statistically significant difference ($p<0.05$).

In FIG. 13A, the tumor accumulation of the example reached a maximum concentration of 5.08% injected dose per gram tissue (ID/g) at 6 hours postadministration. In contrast, a continuous accumulation of the example 4 within 24 hours is revealed by facilitating the dose localization at the tumor via the magnetic navigation, resulting in a 3.6-fold higher % ID/g than the example 3 at 24 hours postadministration. In FIG. 13B, a different biodistribution pattern of the radioisotope between the example 3 and the example 4 is noticed at 24 hours postadministration of the example 3 and the example 4. In FIG. 13C, biodistribution quantitative profiles demonstrate that the example 3 and the example 4 are mostly accumulated at tumor, liver, spleen, and bladder, with minor accumulation at muscle, brain, heart, lung, stomach, kidney, colon, and blood (less than 5% ID/g). More importantly, compared with the example 3, the magnetic navigation in the example 4 not only increases the tumor accumulation, but significantly reduces the systemic accumulation in the liver and the spleen, indicating that the example 4 can be effectively centralized to the site of action.

Figure 13D:
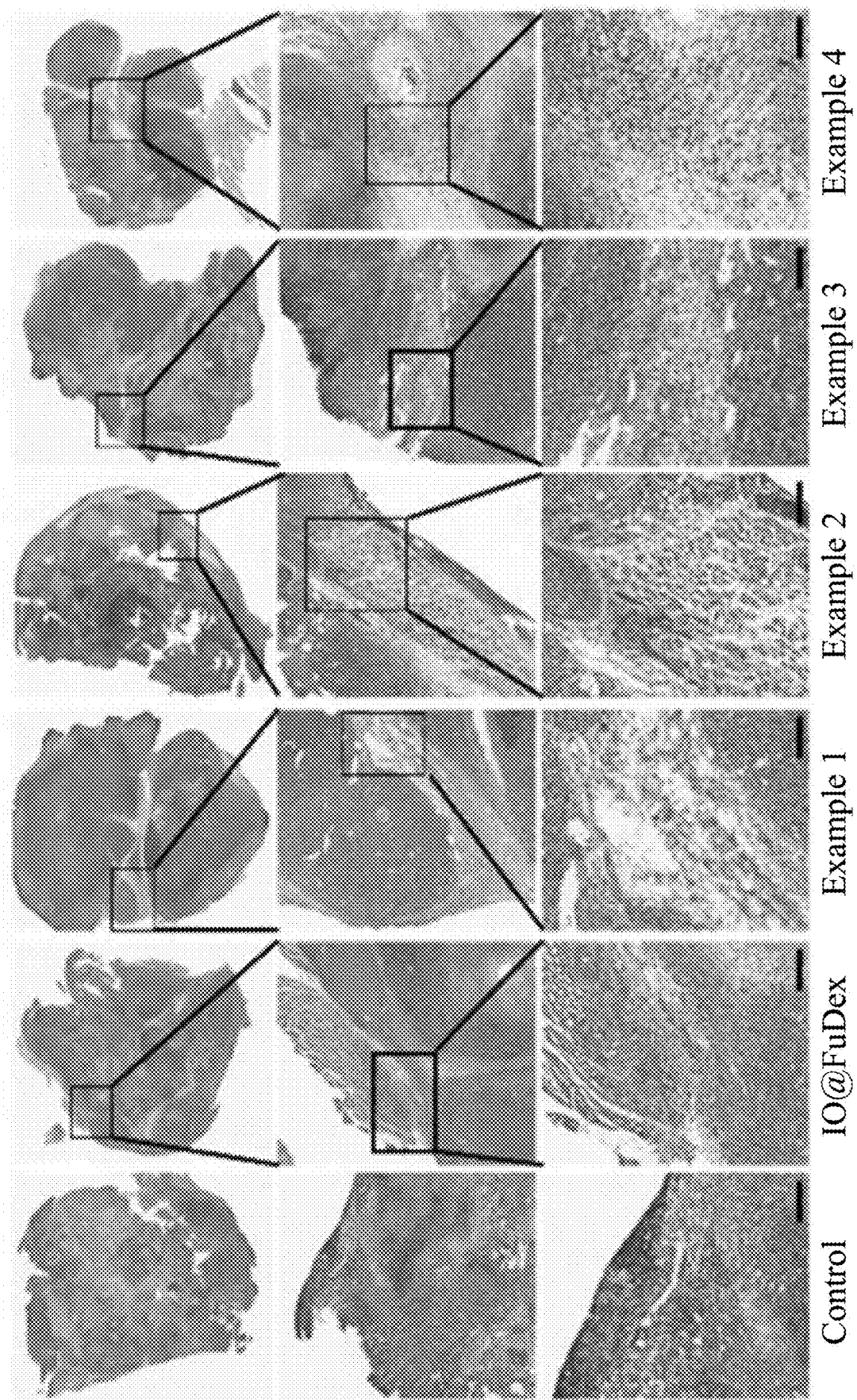
FIG. 13D are hematoxylin and eosin stain with Prussian blue stain photographs showing treatment effect of a pharmaceutical composition for treating cancer and the kit for treating cancer of the present disclosure.

In this experiment, the 4T1-Luc tumor-bearing mice are further administrated the IgG (control), the IO@FuDex and the examples 1-4 via the right femoral vein. The administrations are started on day 8 after tumor implantation. The administration method is three times at intervals of 4 days (q4d×3). FIG. 13D shows hematoxylin and eosin stain with Prussian blue stain photographs of the 4T1-Luc tumor-bearing mice at 24 hours postadministration of the examples 1-4, wherein the scale represents the length of 50 μm. In FIG. 13D, dispersed Prussian blue stains can be observed in the tumor tissue with the example 4 administration compared to other examples.

To confirm the therapeutic effect of the pharmaceutical composition for treating cancer and the kit for treating cancer of the present disclosure have the therapeutic effect on the 4T1-Luc tumor-bearing mice, the 4T1-Luc tumor-bearing mice are further administrated the IgG (control), the IO@FuDex and the examples 1-4 via the right femoral vein. The administration was started on day 8 after tumor implantation. The administration method is three times at intervals of 4 days (q4d×3). The tumor volumes are monitored using a digital caliper (Mitutoyo) every 2 to 3 days using the following Equation I:

$$\text{Tumor volume (mm}^3) = \frac{W^2 \times L}{2};\qquad \text{Equation I}$$

where W is the width of the tumor and L is the length of the tumor (W<L). The bioluminescence assessment is analyzed by a non-invasion in vivo imaging system (IVIS 200 System, Xenogen). The survival rate of the 4T1-Luc tumor-bearing mice is analyzed using Kaplan-Meier survival analysis.

Figure 14A:
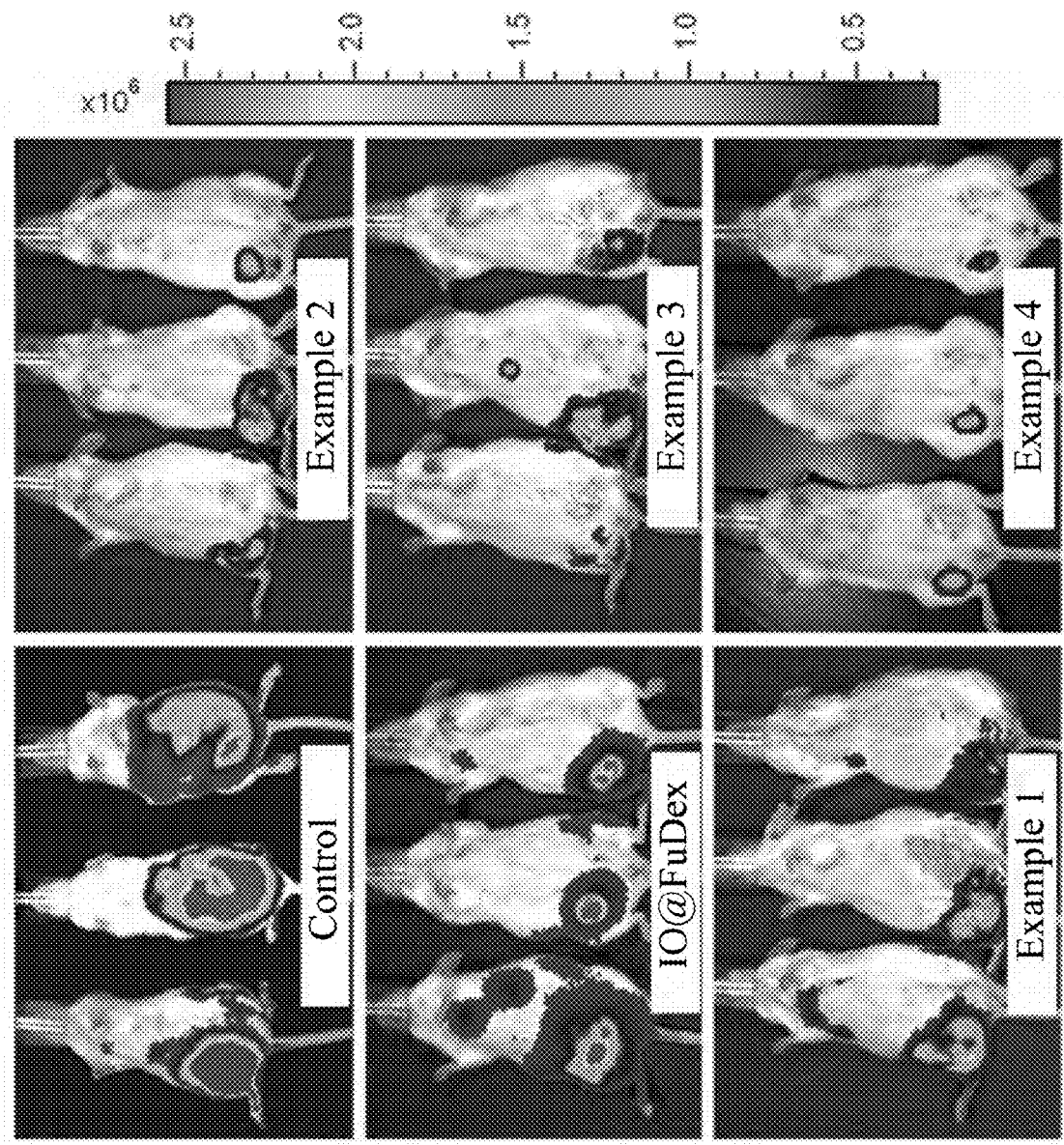
FIGS. 14A, 14B, 14C, 14D and 14E show analysis results of cancer cell proliferation inhibiting capacity and anti-metastasis capacity in a breast cancer metastasis mouse model of the pharmaceutical composition for treating cancer and the kit for treating cancer of the present disclosure.
Figure 14B:
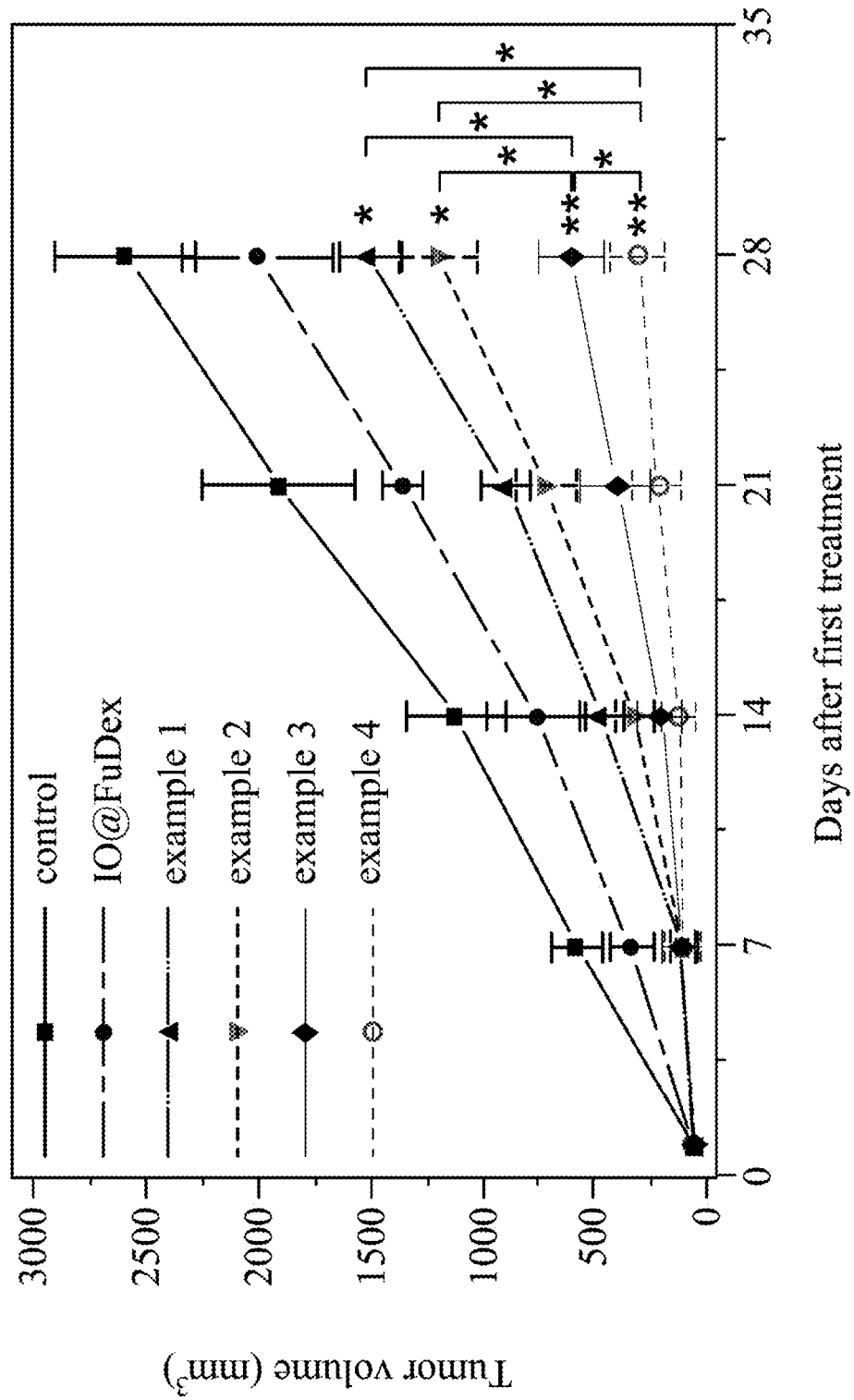
Figure 14C:
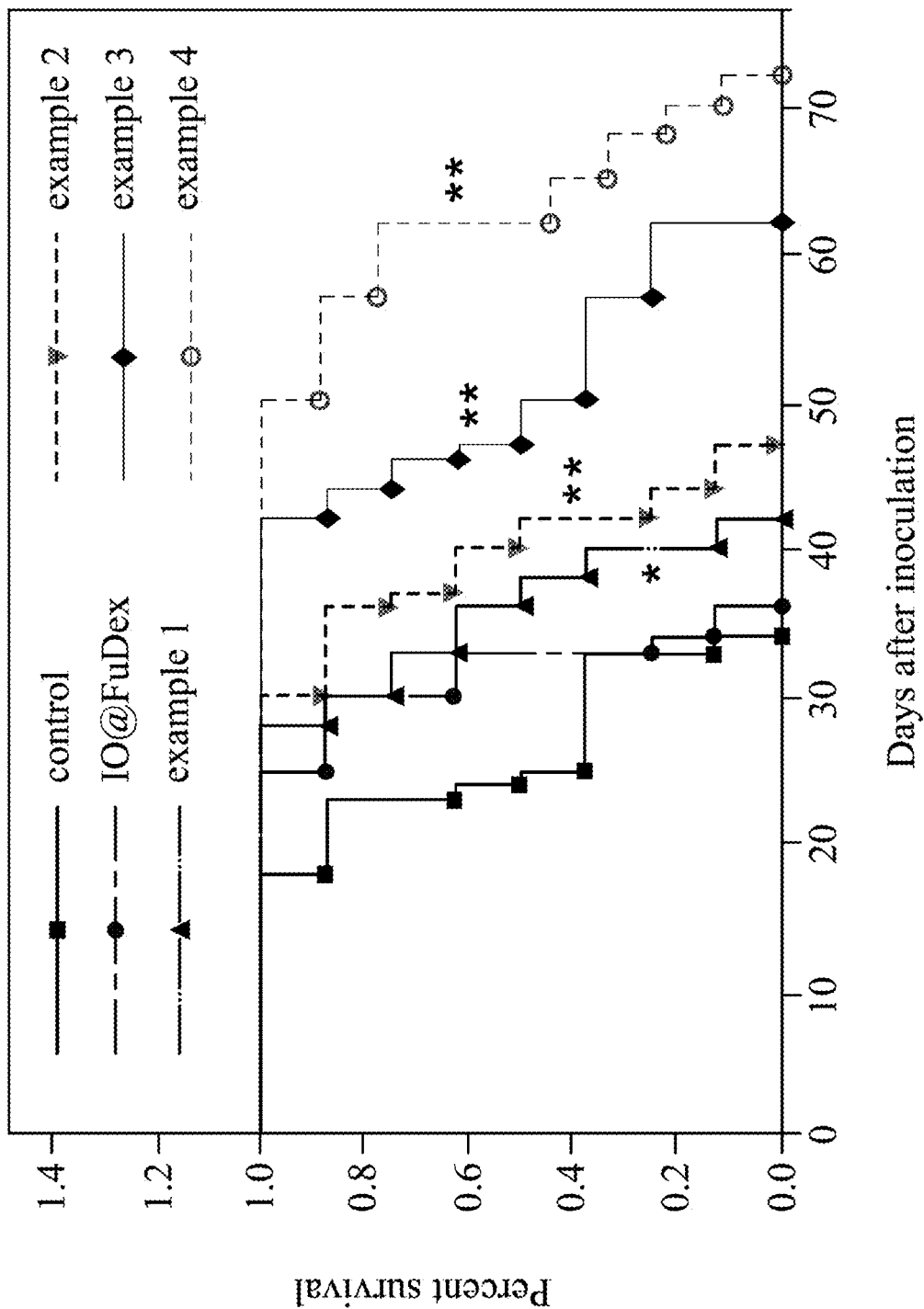
Figure 14D:
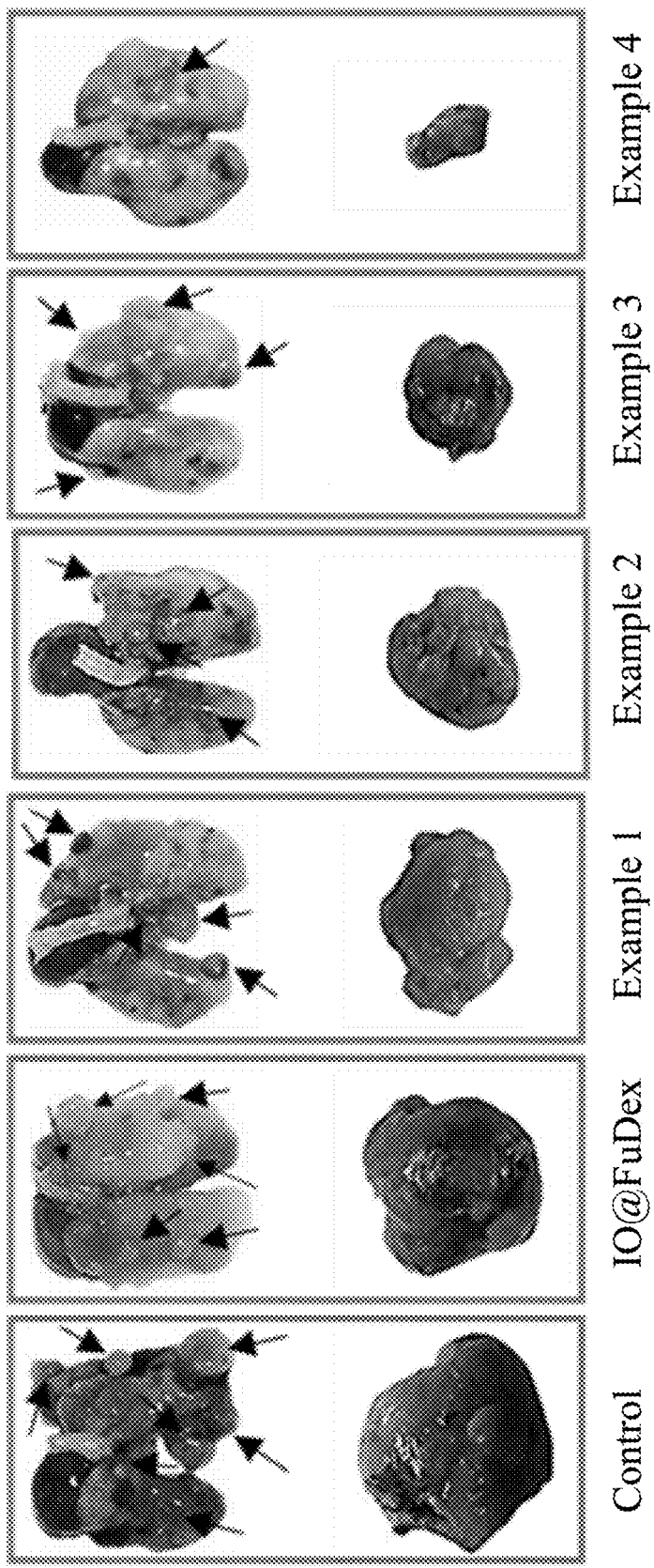
Figure 14E:
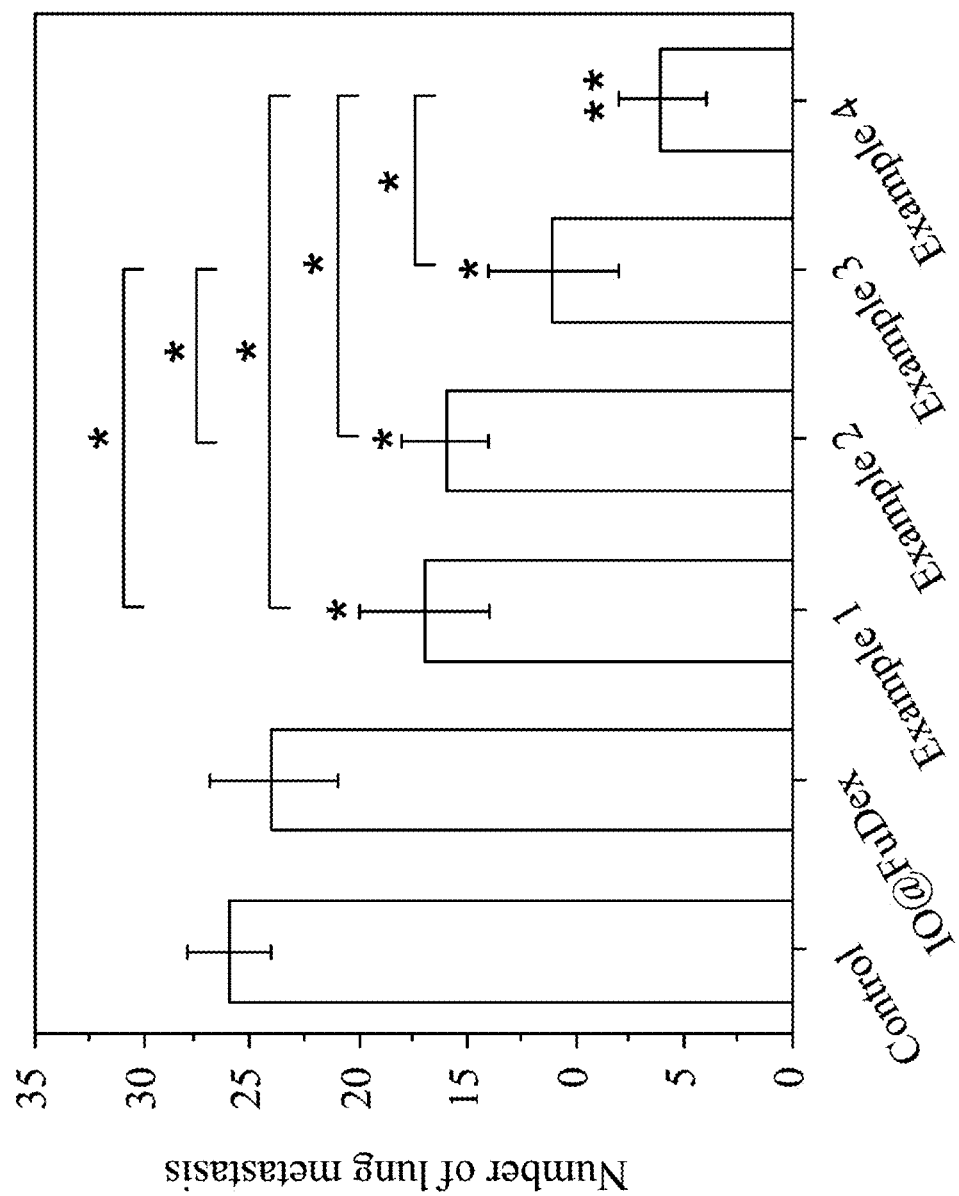

Please refer to FIGS. 14A to 14E, which show analysis results of cancer cell proliferation inhibiting capacity and anti-metastasis capacity in the 4T1-Luc tumor-bearing mice of the pharmaceutical composition for treating cancer and the kit for treating cancer of the present disclosure. FIG. 14A shows the IVIS system scanning images of the 4T1-Luc tumor-bearing mice at 24 hours postadministration of the examples 1-4. FIG. 14B is a chart showing tumor volume of the 4T1-Luc tumor-bearing mice administrated the examples 1-4. FIG. 14C shows survival curves of the 4T1-Luc tumor-bearing mice administrated the examples 1-4. FIG. 14D shows pictures of dissected tumors and lungs of the 4T1-Luc tumor-bearing mice administrated the examples 1-4. FIG. 14E is a chart showing lung metastases of the 4T1-Luc tumor-bearing mice administrated the examples 1-4.

In FIGS. 14A and 14B, the IO@FuDex exhibited therapeutic effect on reducing tumor volumes compared to control group, but there is no statistically significant difference. The examples 1-4 show stronger anti-tumor effects with statistically significant difference (* represents $p<0.05$ and ** represents $p<0.01$), where the example 4 nearly inhibited tumor growth in 30 days. In FIG. 14C, the median survival time of the 4T1-Luc tumor-bearing mice administrated with the IgG, the IO@FuDex, the example 1, the example 2, and the example 3 are 24 days, 34 days, 34 days, 43 days and 44 days, while the median survival time of the 4T1-Luc tumor-bearing mice administrated with the example 4 significantly extends to 63 days. Although the dose of the PD-L1 antibody in the example 4 is only one percent of the dose of pure antibody administered in general, the example 4 is able to exhibit more excellent tumor inhibiting ability and extend the half-life by more than 2 times. Furthermore, the results in FIG. 14D indicate that all the examples exhibit anti-metastasis ability. As shown in FIG. 14D, the example 3 and the example 4 significantly prevent the tumor metastasis in lungs compared with other groups. In FIG. 14E, on average, fewer than 5 nodules of lung metastasis are discovered in the example 4 administrated 4T1-Luc tumor-bearing mice compared to over 20 metastases in lungs of the control administrated 4T1-Luc tumor-bearing mice. Thus, the administration including the pharmaceutical composition for treating cancer and the kit for treating cancer of the present disclosure evidently provide both tumor inhibition and anti-metastasis effect. However, the IO@FuDex does not show significant decrease in metastasis compared to the control group. As a result, we hypothesize that the anti-metastasis effect of the pharmaceutical composition for treating cancer and the kit for treating cancer of the present disclosure is not only inhibited by fucoidan but largely affected by the dynamic reactions in the tumor microenvironment.

2.1.2 Therapeutic Effect of the Pharmaceutical Composition for Treating Cancer of the Present Disclosure on Treatment of Colorectal Cancer The CT-26 cell lines with the luciferase gene that stably express the biological luminescent enzyme (provided by the Center for Molecular Medicine, University Hospital of China Medical University) are utilized for building the colorectal cancer mouse model in this experiment. The IgG (control), the IO@FuDex and the pharmaceutical composition for treating cancer including the $I^{125}$-labeled example 3 is administered via the right femoral vein to the CT-26 tumor-bearing mice, respectively. The example 4, which includes the $I^{125}$-labeled example 3 and the superficial round-shape magnet (diameter=0.5 cm, 0.5 Tesla) for the magnetic navigation, is included in this experiment as the kit for treating cancer. In addition, the IO@FuDex cooperated with the superficial round-shape magnet for the magnetic navigation is included in this experiment as a comparative example 1. The administrations are started on day 8 after tumor implantation. The administration method is three times at intervals of 4 days (q4d×3). The tumor volumes are monitored using a digital caliper (Mitutoyo) every 2 to 3 days using the Equation I. The bioluminescence assessment is analyzed by the IVIS System. The survival rate of the CT-26 tumor-bearing mice is analyzed using Kaplan-Meier survival analysis.

Figure 15A:
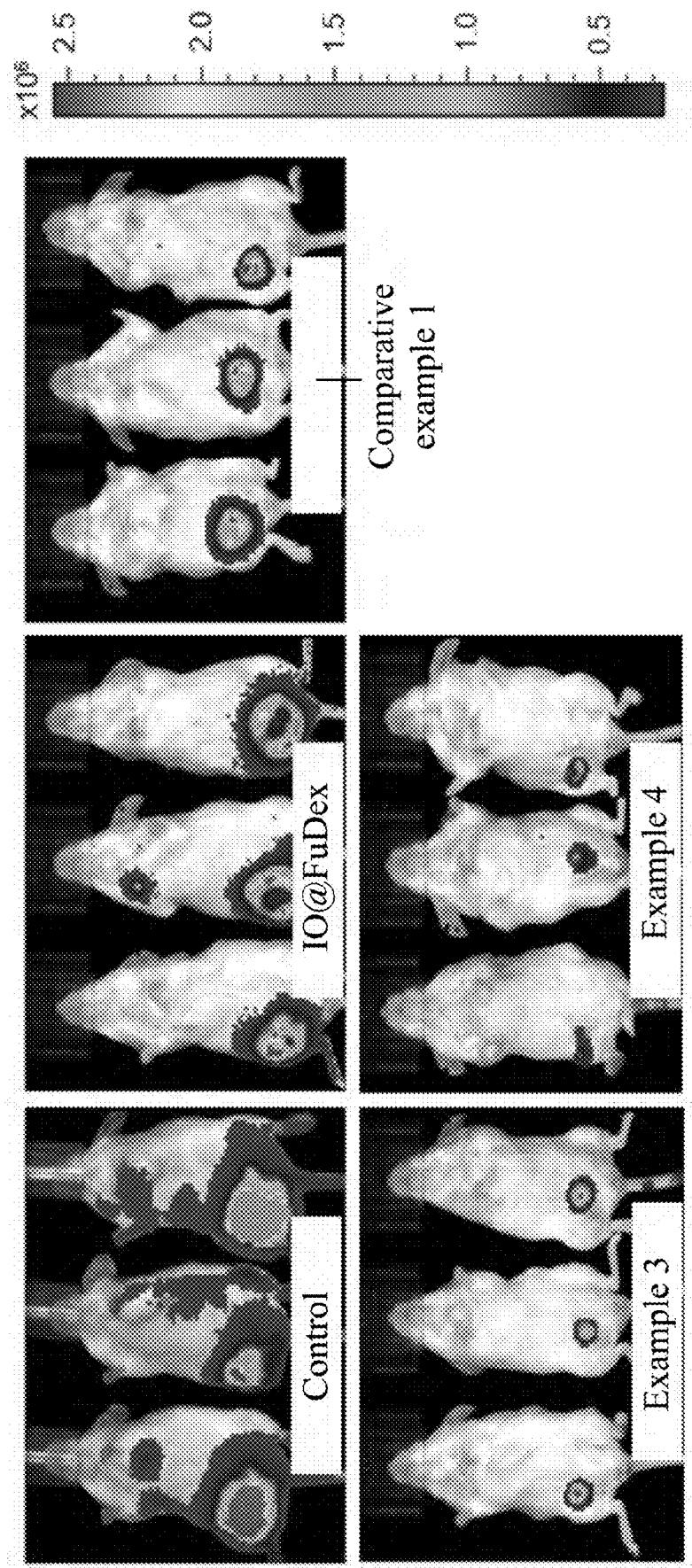
FIGS. 15A, 15B and 15C show analysis results of cancer cell proliferation inhibiting capacity in a colorectal cancer mouse model of the pharmaceutical composition for treating cancer and the kit for treating cancer of the present disclosure.
Figure 15B:
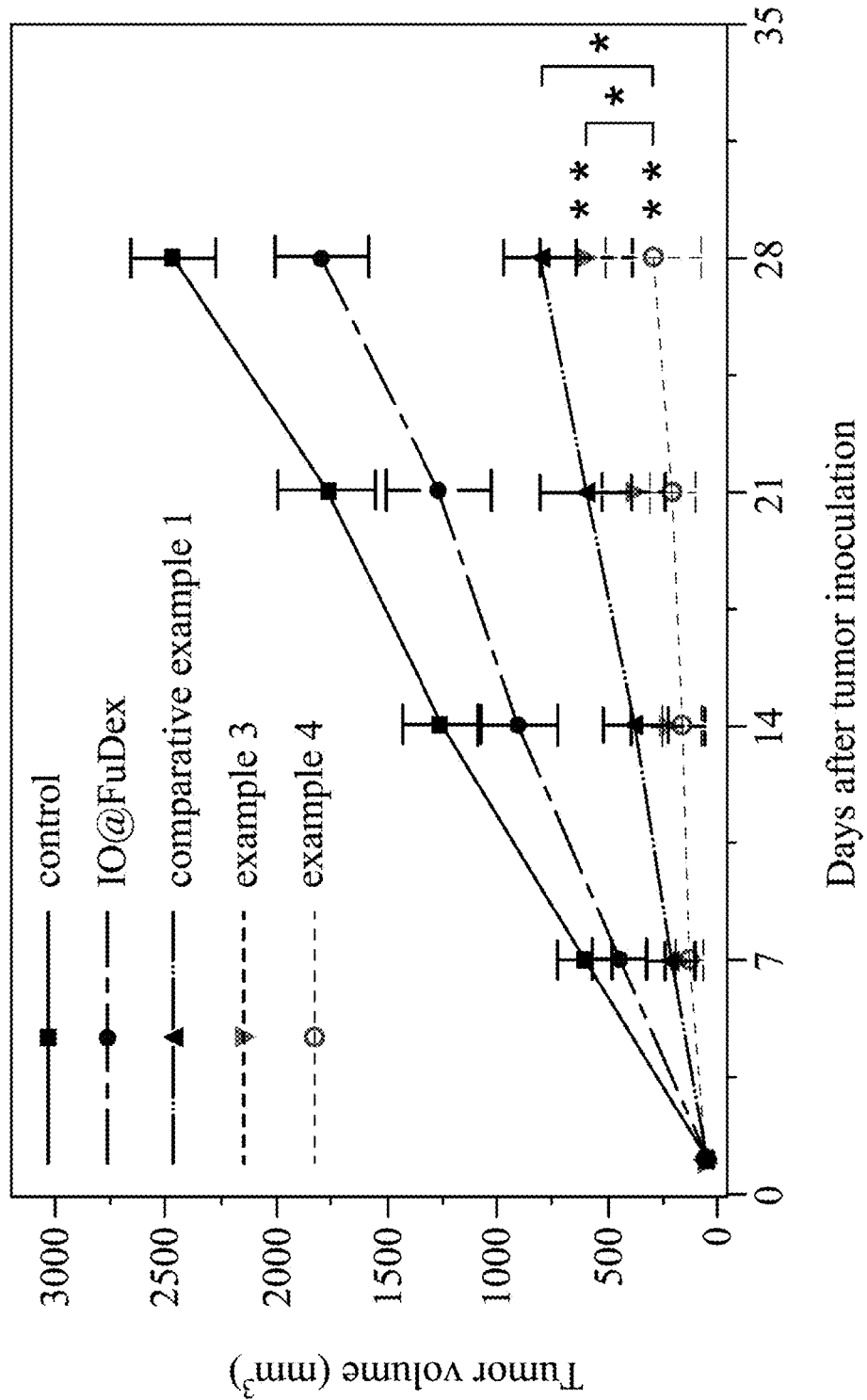
Figure 15C:
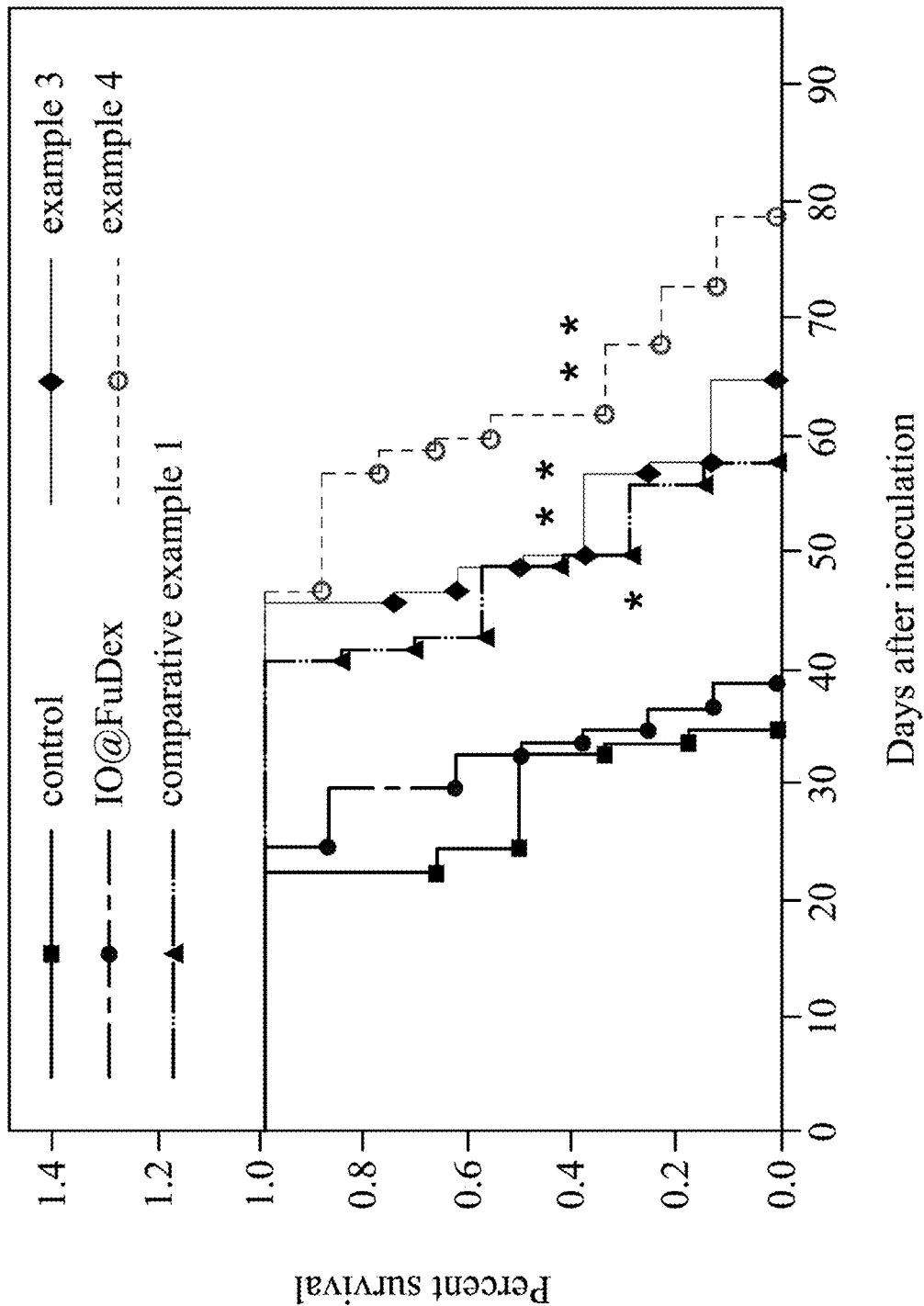

Please refer to FIGS. 15A to 15C, which show analysis results of cancer cell proliferation inhibiting capacity in the colorectal cancer mouse model of the pharmaceutical composition for treating cancer and the kit for treating cancer of the present disclosure. FIG. 15A shows the IVIS system scanning images of the CT-26 tumor-bearing mice at 24 hours postadministration of the examples 3-4. FIG. 15B is a chart showing tumor volume of the CT-26 tumor-bearing mice administrated the examples 3-4. FIG. 15C shows survival curves of the CT-26 tumor-bearing mice administrated the examples 3-4.

In FIGS. 15A and 15B, the IO@FuDex reduces the tumor volumes compared to control group, but there is no statistically significant difference. The comparative example 1, which administrates the IO@FuDex cooperated with the magnetic navigation, can increase the therapeutic effect of the IO@FuDex. The example 3 and example 4 show stronger anti-tumor effects with statistically significant difference (* represents $p<0.05$ and ** represents $p<0.01$), where the example 4 nearly inhibited tumor growth in 30 days. In FIG. 15C, the administration of the example 3 and the example 4 significantly prolongs the survival time of the CT-26 tumor-bearing mice. These results indicate the tumor inhibiting ability and the anti-metastasis effect of the pharmaceutical composition for treating cancer and the kit for treating cancer of the present disclosure again.

2.2 Analysis of Immune Activation after Administration of the Pharmaceutical Composition for Treating Cancer and the Kit for Treating Cancer of the Present Disclosure The 4T1-Luc tumor-bearing mice is further used in this experiment to investigate the immune activation of the pharmaceutical composition for treating cancer and the kit for treating cancer of the present disclosure in the tumor microenvironment. The changes in the frequency of leukocytes in tumors, blood, ascites and spleens of the 4T1-Luc tumor-bearing mice from early (10 days) to late times of tumor growth (30 days) are monitored.

Figure 16B:
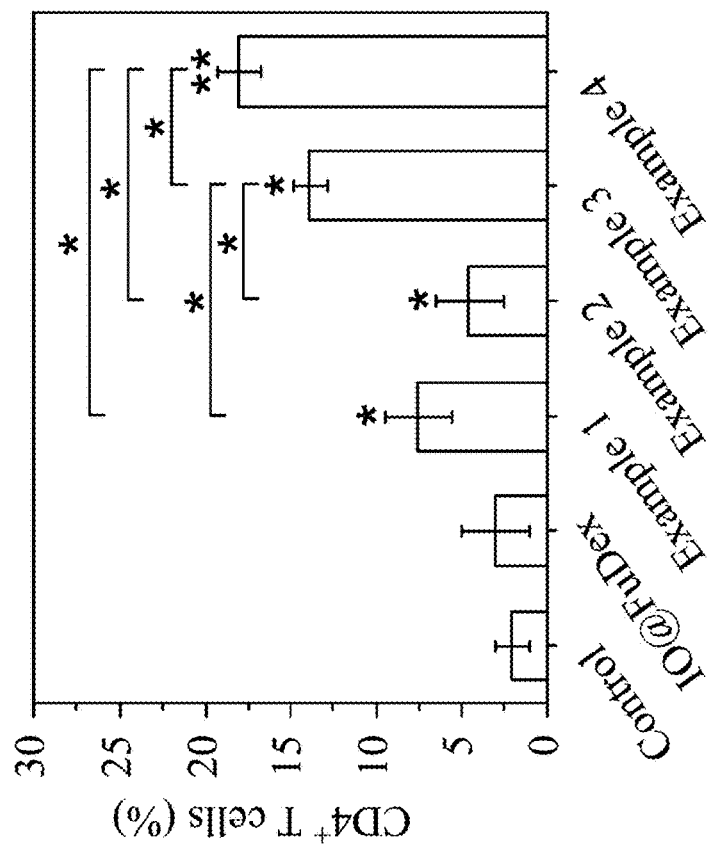
FIGS. 16A, 16B, 16C, 16D, 16E, 16F, 16G, 16H and 16I show analysis results of changes of tumor-infiltrating lymphocytes and cytokines in tumor microenvironment after administering the pharmaceutical composition for treating cancer and the kit for treating cancer of the present disclosure.
Figure 16A:
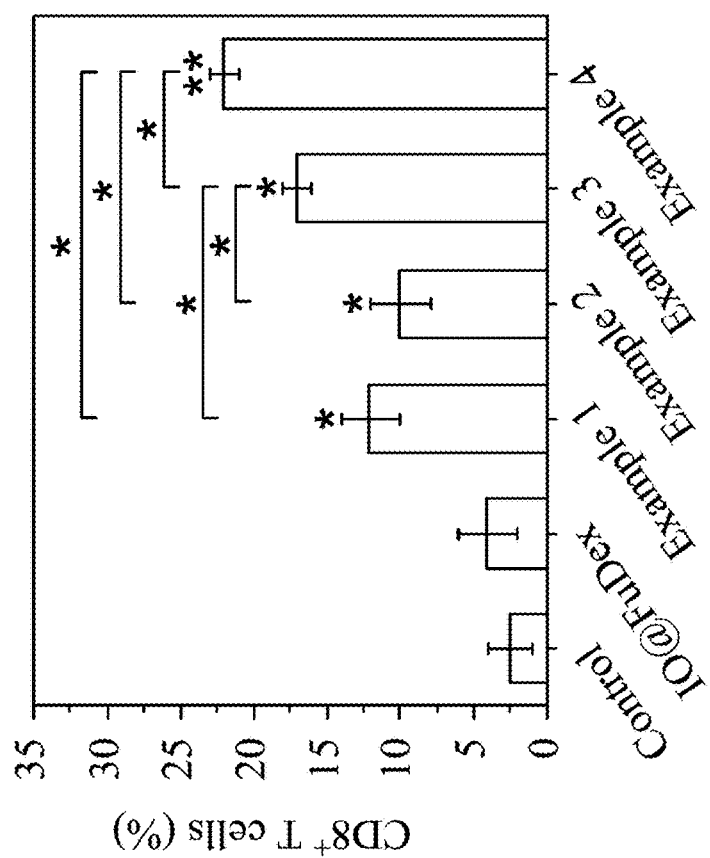
Figure 16D:
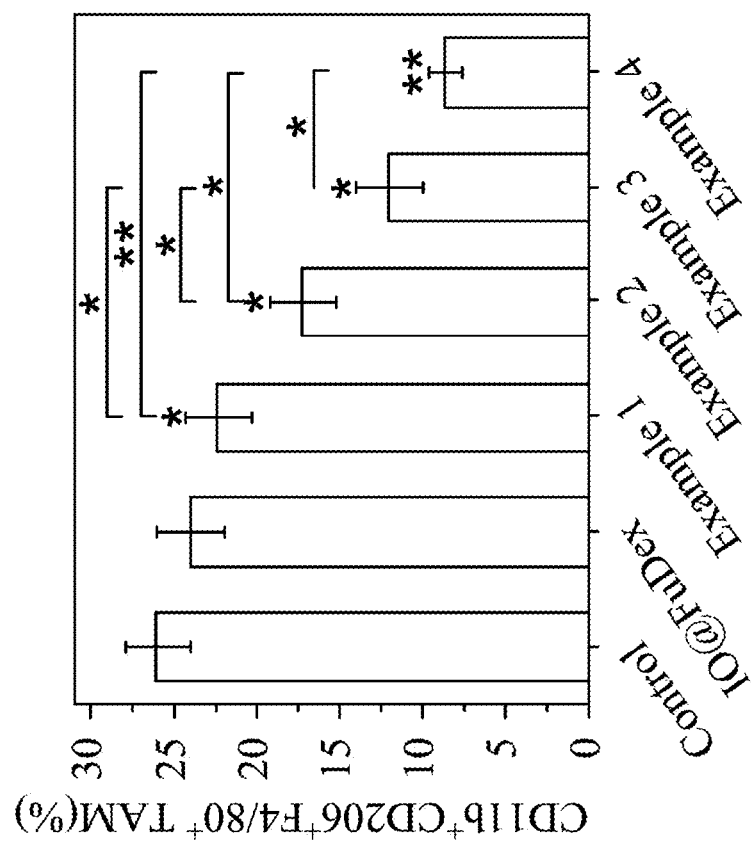
Figure 16C:
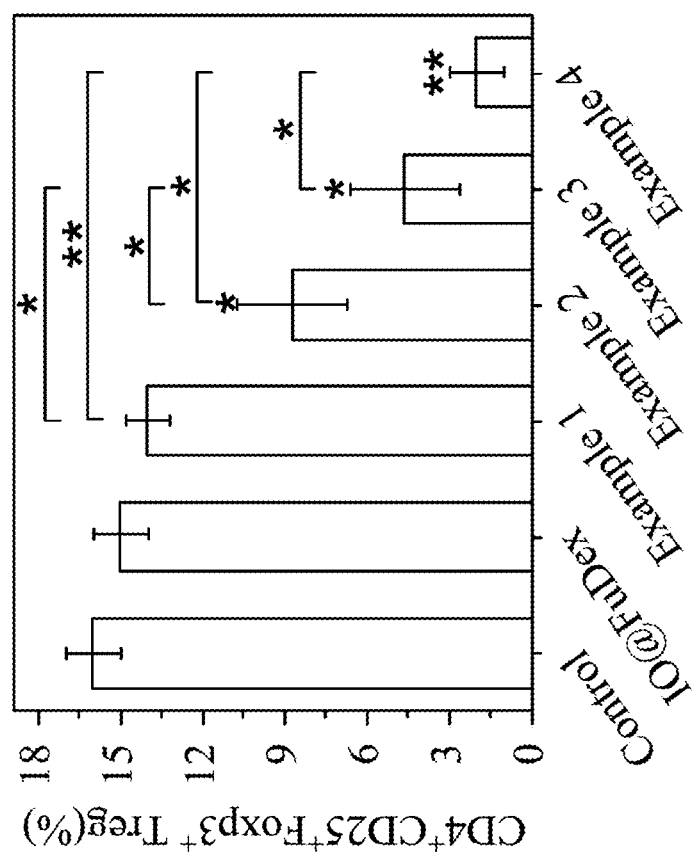
Figure 16F:
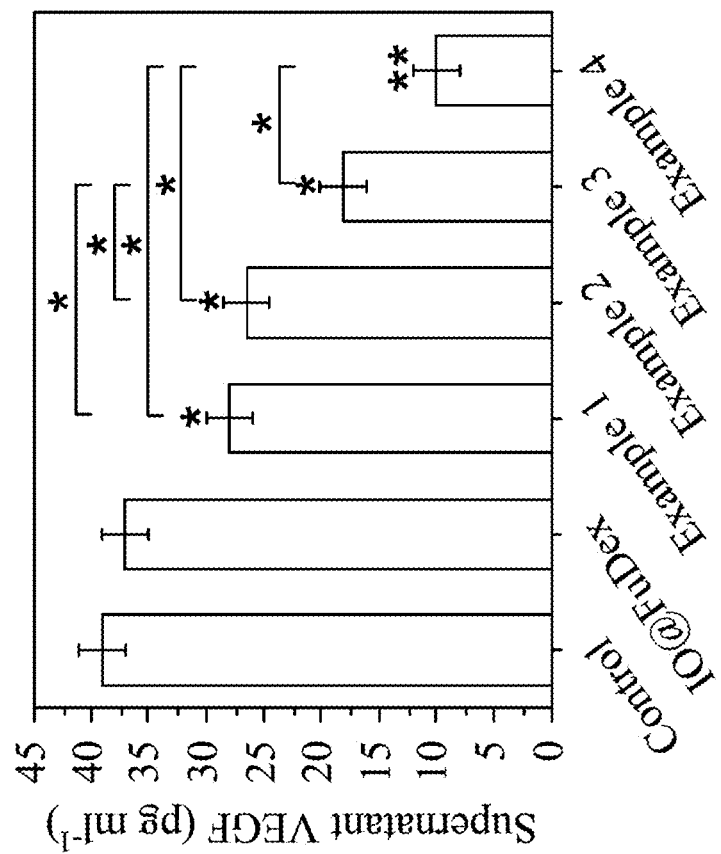
Figure 16E:
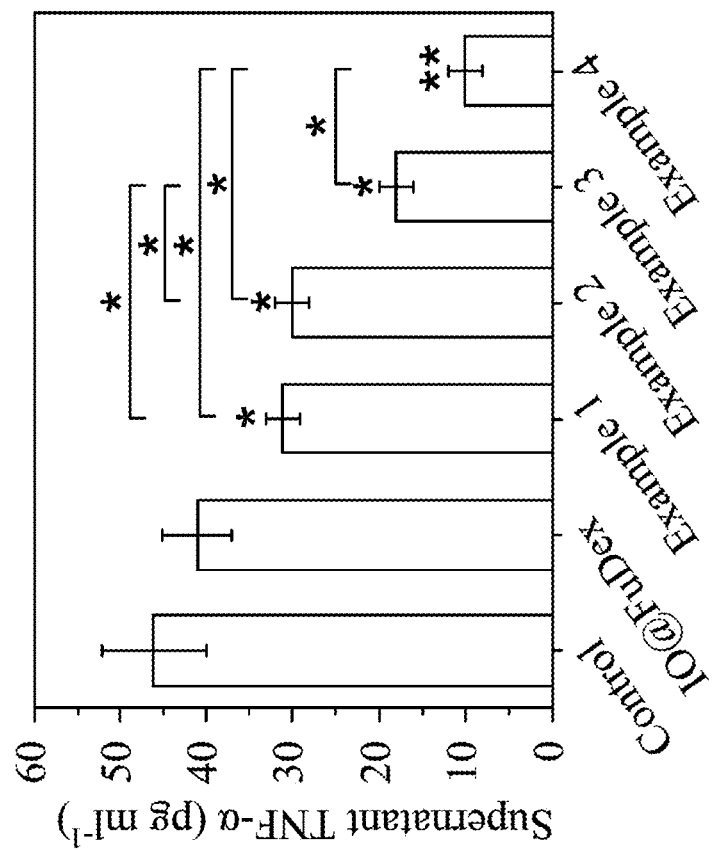
Figure 16H:
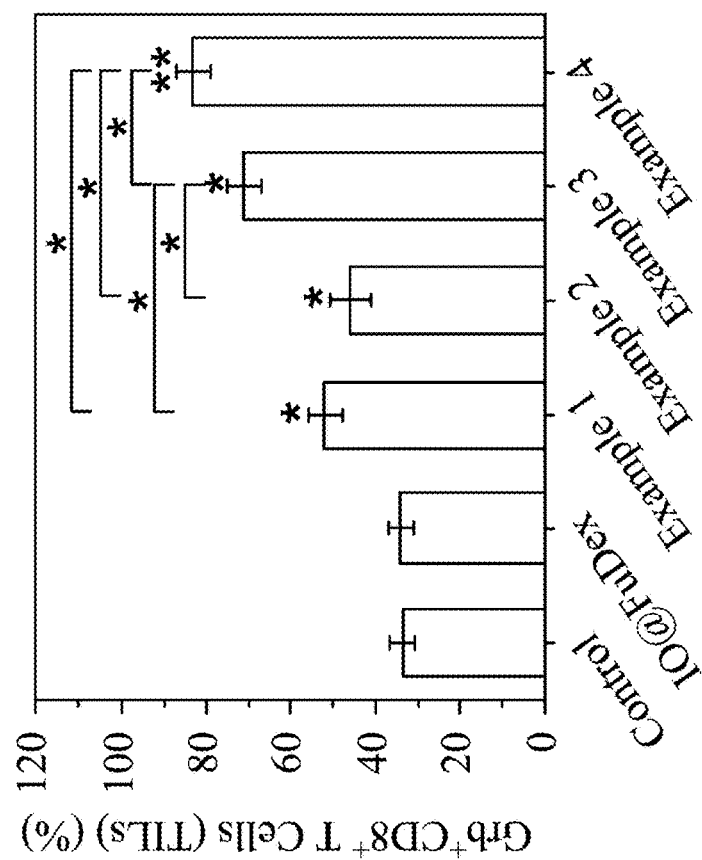
Figure 16G:
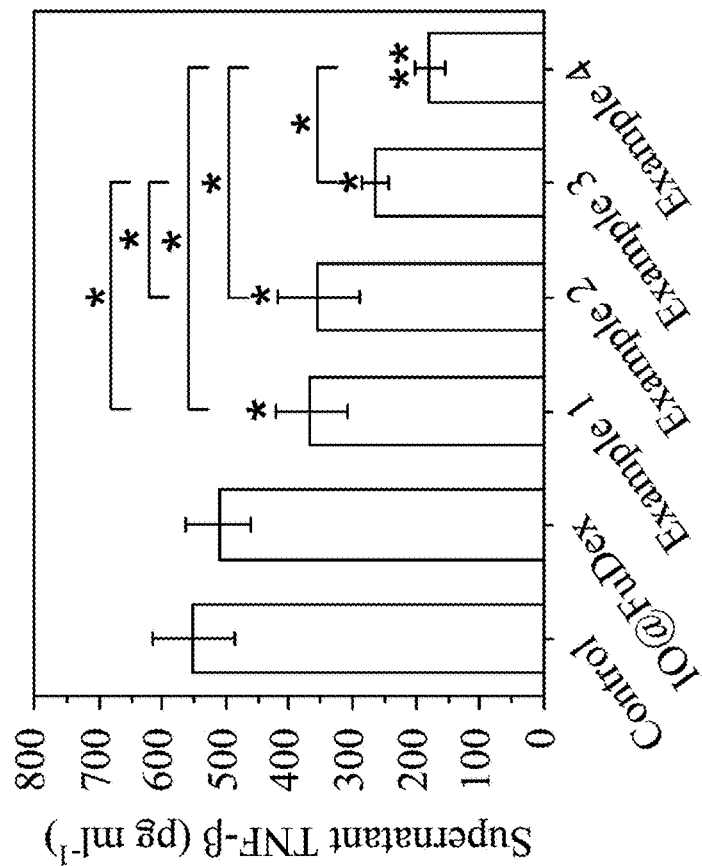
Figure 16I:
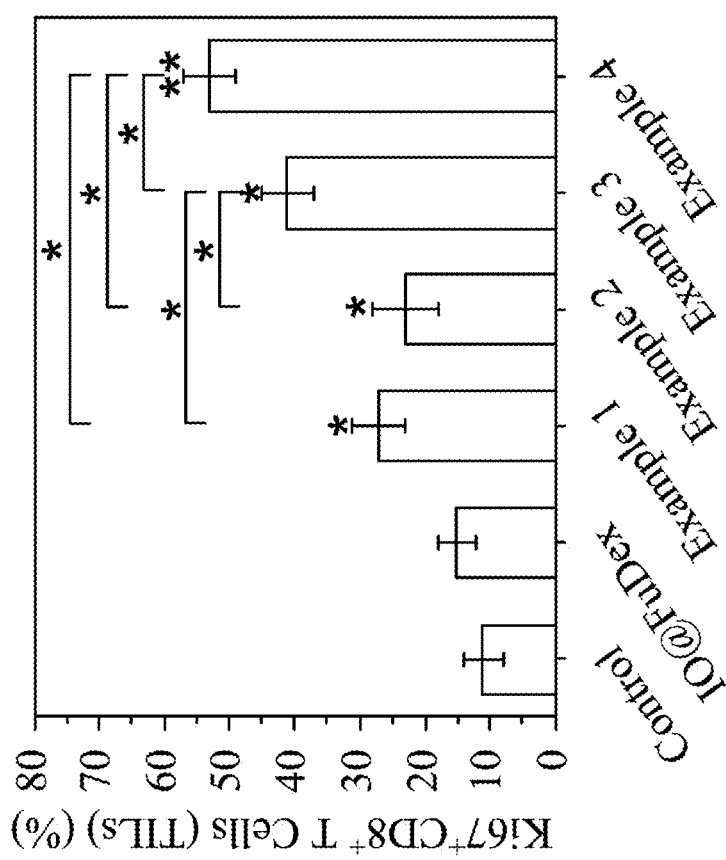

Please refer to FIGS. 16A to 16I, which show analysis results of changes of tumor-infiltrating lymphocytes and cytokines in tumor microenvironment after administering the pharmaceutical composition for treating cancer and the kit for treating cancer of the present disclosure. In FIGS. 16A and 16B, the number of antitumor lymphocytes, such as $CD8^+$ T cells and $CD4^+$ T cells, is significantly increased in the groups administrated the examples 1-4; in particularly in the group administered with the example 4 ($p<0.01$). In FIGS. 16C and 16D, the number of pro-tumor antitumor lymphocytes, such as $CD4^+CD225^+Foxp3^+$ Tregs (regulatory T cells) and $CD11b^+CD206^+F4/80^+$ TAM (tumor associated macrophages), is significantly reduced in the groups administrated the examples 1-4, especially the group administered with the example 4 can drastically reduce the number of regulatory T cells (Treg) ($p<0.01$). Different groups of the 4T1-Luc tumor-bearing mice sera are collected to analyze the levels of TNF-α, VEGF and TGF-β, secreted by the TAM. In FIG. 16E to 16G, the levels of the pro-inflammatory cytokines such as the TNF-α, the VEGF and the TGF-β can be significantly reduced in the groups administrated the examples 1-4; in particularly in the group administered with the example 4 ($p<0.01$). In FIGS. 16H and 16I, the degree of $CD8^+$ T cells activation is assessed by the expression levels of intragranular granzyme B ($GrB^+$) and Ki67. Upregulations of intracellular granzyme B ($Grb^+$) and $Ki67^+$ $CD8^+$ T cells in the groups administrated with the examples 1-4 indicate that the examples 1-4 effectively activated $CD8^+$ TILs functions, especially the group administered with the example 4 ($p<0.01$).

The aforementioned experiments demonstrate that the administration of the pharmaceutical composition for treating cancer and the kit for treating cancer of the present disclosure can change the tumor microenvironment. In this experiment further assesses the change in tumor-specific immune response and systemic effects after administrating the pharmaceutical composition for treating cancer and the kit for treating cancer of the present disclosure. Tumors, sera and spleens of different groups of the 4T1-Luc tumor-bearing mice are collected to analyze the changes of INF-$\gamma^+CD44^+$ T cells and $CD8^+CD3^+$ T cells. The apoptosis of skin tissue of the 4T1-Luc tumor-bearing mice in different groups are analyzed by a TUNEL assay.

Figure 17A:
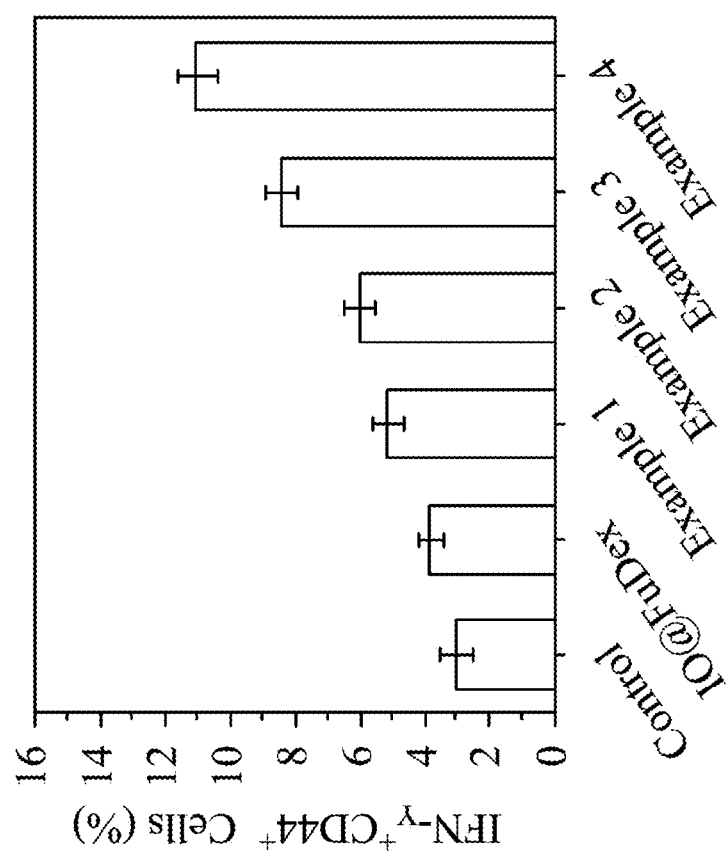
FIGS. 17A and 17B show reaction sites analysis results of the pharmaceutical composition for treating cancer and the kit for treating cancer of the present disclosure.
Figure 17B:
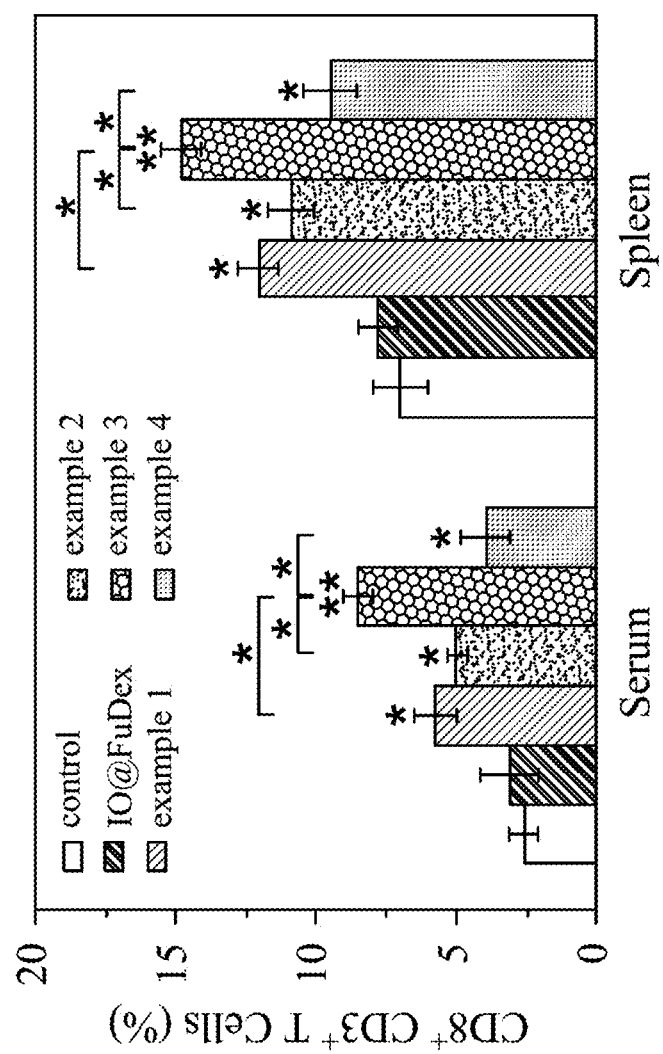

Please refer to FIGS. 17A and 17B, which show reaction sites analysis results of the pharmaceutical composition for treating cancer and the kit for treating cancer of the present disclosure. FIG. 17A shows the results of changes in INF-$\gamma^+CD44^+$ T cells from different groups of the 4T1-Luc tumor-bearing mice. FIG. 17B shows the results of changes in $CD8^+CD3^+$ T cells from different groups of the 4T1-Luc tumor-bearing mice.

In FIG. 17A, the proliferation number of INF-$\gamma^+CD44^+$ T cells is increased in the groups administrated with the examples 1-4; in particularly in the group administered with the example 4. In FIG. 17B, the $CD8^+CD3^+$ T cells are proliferated in both the serum and the spleen after administrating the examples 1-3. When compared the group administered with the example 4 to the group administered with the example 3, the magnetic navigation reduces the proliferation of the $CD8^+CD3^+$ T cells in the serum and the spleen.

Cutaneous toxicity induced pruritus and vitiligo is one of the adverse effect found in the immune checkpoint inhibitor therapy. Since immune-related adverse events are often appear in long-term condition, the TUNEL assay is performed in the skin tissues of the 4T1-Luc tumor-bearing mice at 4 weeks after first dose to evaluate whether these infiltrated T cells induce immune response and cause tissue damage in skin.

Figure 17C:
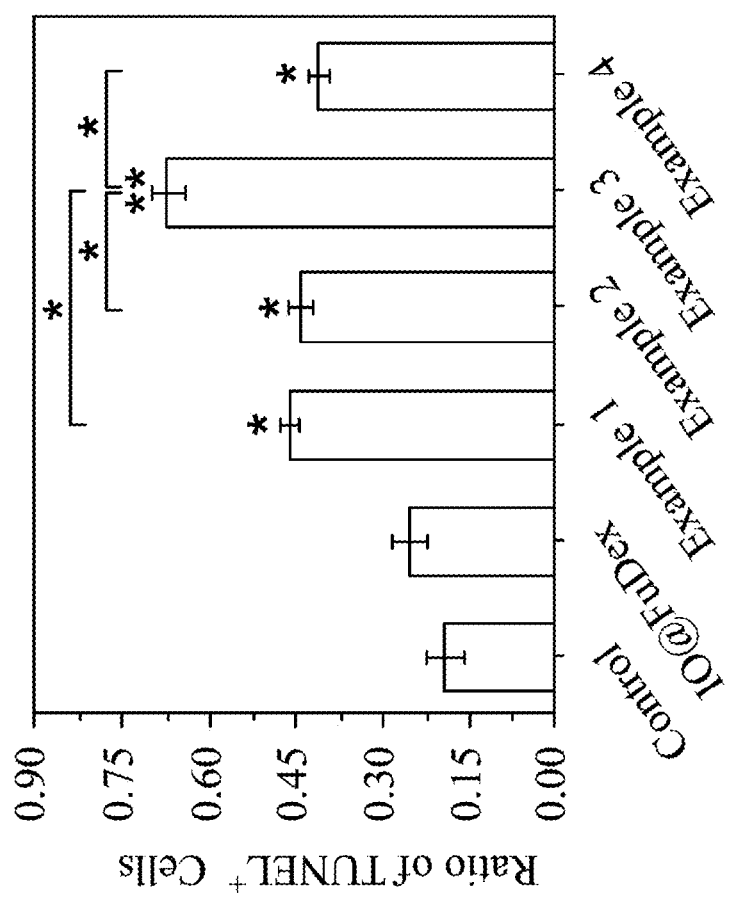
FIGS. 17C and 17D show TUNEL analysis results of the pharmaceutical composition for treating cancer and the kit for treating cancer of the present disclosure.
Figure 17D:
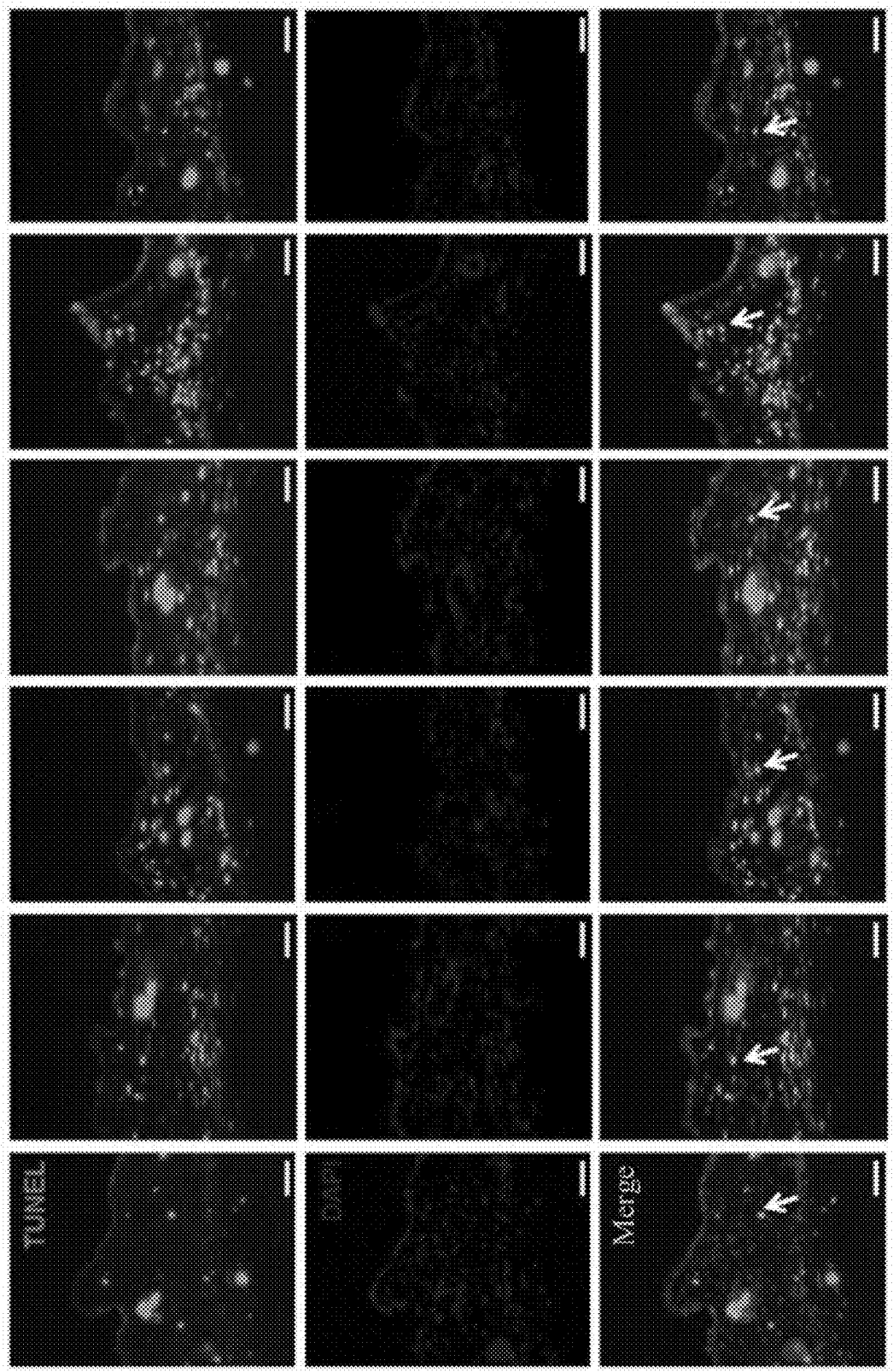

Please refer to FIGS. 17C and 17D, which show TUNEL assay results of the pharmaceutical composition for treating cancer and the kit for treating cancer of the present disclosure. FIG. 17C shows the statistical results of the apoptotic index of the skin measured by TUNEL in different groups of the 4T1-Luc tumor-bearing mice, wherein the apoptotic index stands as the ratio of $TUNEL^+$ apoptotic nuclei divided by the total number of nuclei which is counter-stained using DAPI from randomly chosen microscopic fields. Differences between groups are evaluated by two-way ANOVA with the Newman-Keuls post hoc test. FIG. 17D shows fluorescent micrographs of the TUNEL assay of the different groups of the 4T1-Luc tumor-bearing mice, where the scale bar represents the length of 50 μm.

In FIGS. 17C and 17D, TUNEL-labeled (green) apoptotic cells are increased in the groups administrated with the examples 1-3, wherein the apoptotic index of the group administrated with the example 3 induced a 3.3-fold increase compared to the control group. However, when compared the group administered with the example 4 to the group administered with the example 3, the magnetic navigation effectively reduces the number of apoptotic cells in the skin tissue.

2.3 Analysis of Immune-Related Adverse Events after Administration of the Pharmaceutical Composition for Treating Cancer and the Kit for Treating Cancer of the Present Disclosure To analyze the safety of the pharmaceutical composition for treating cancer and the kit for treating cancer of the present disclosure, the 4T1-Luc tumor-bearing mice are administrated with the example 3 (the pharmaceutical composition for treating cancer of the present disclosure) and the example 4 (the kit for treating cancer of the present of disclosure), respectively, in this experiment. The analysis of the Immune-related adverse events (irAE s) in the 4T1-Luc tumor-bearing mice is performed at 4 weeks after the tumor implantation.

Figure 18A:
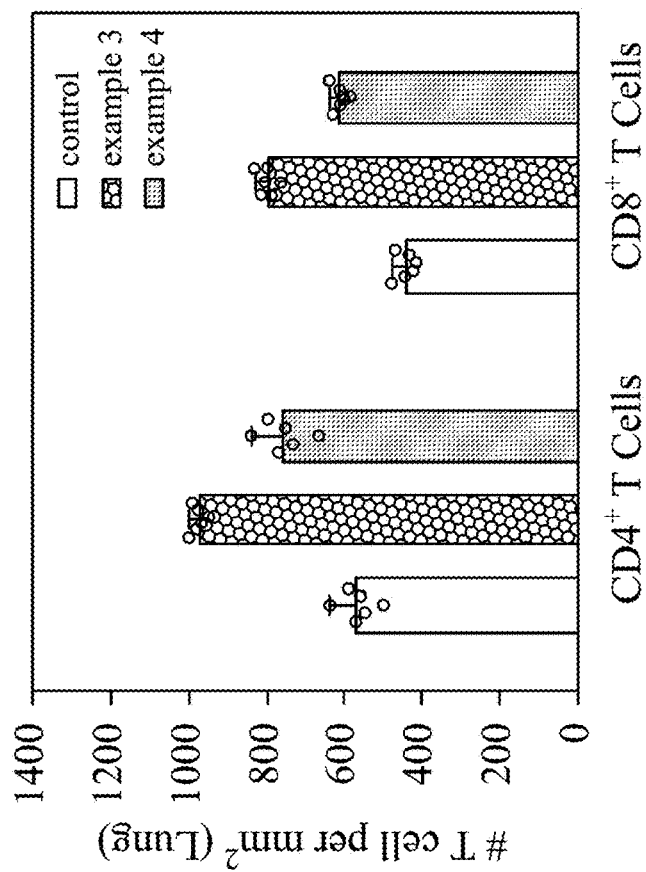
FIGS. 18A, 18B, 18C, 18D and 18E show analysis results of infiltration degree of $CD4^+$ T cells and $CD8^+$ T cells of mice after administering the pharmaceutical composition for treating cancer and the kit for treating cancer of the present disclosure.
Figure 18B:
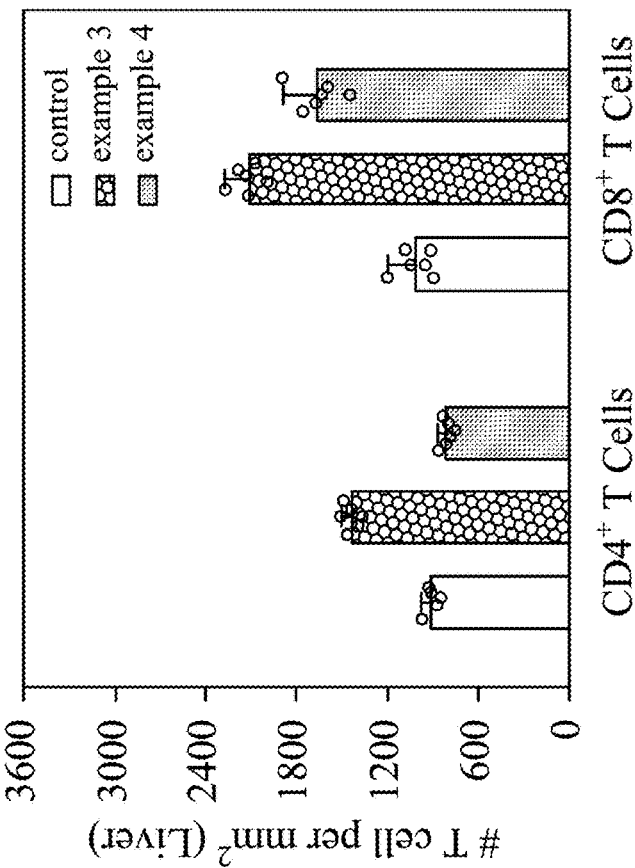
Figure 18D:
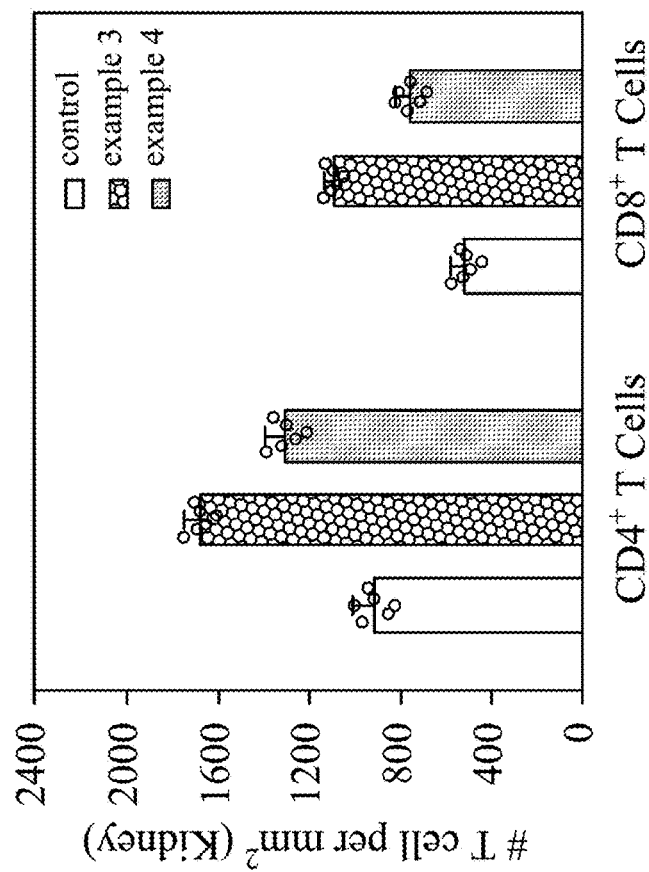
Figure 18C:
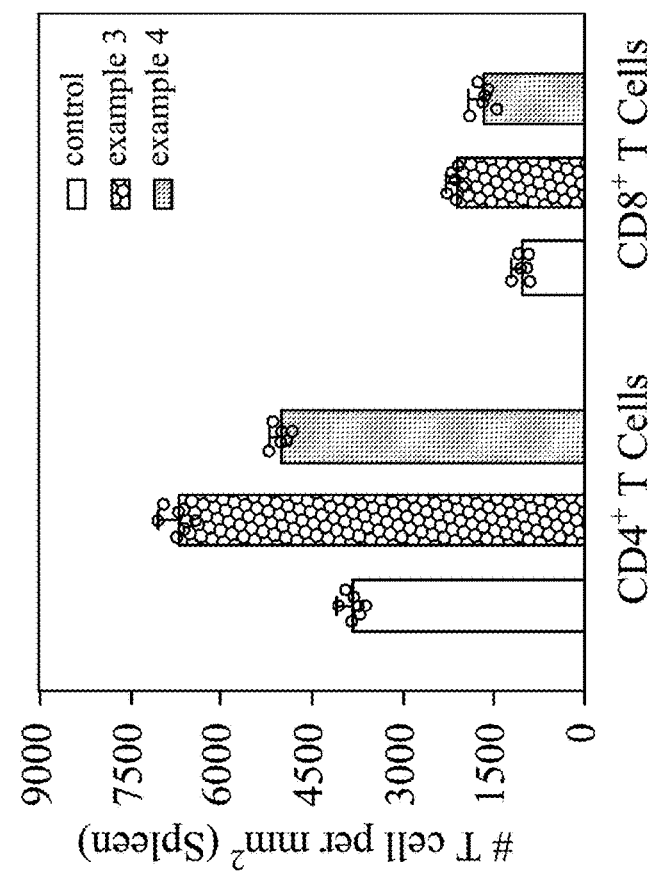
Figure 18E:
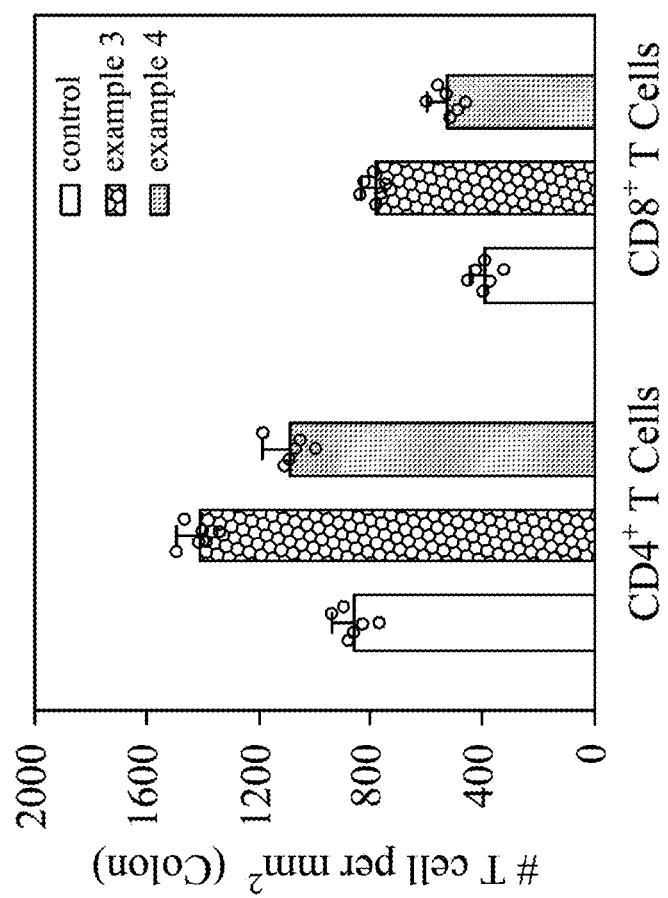

In this experiment, the effect of side effects are determined by observing the infiltration degree of the $CD4^+$ T cells and the $CD8^+$ T cells in major organs of the 4T1-Luc tumor-bearing mice at 4 weeks postadministration of the examples 3 or the example 4. Please refer to FIGS. 18A to 18E, which are analysis results of infiltration degree of $CD4^+$ T cells and $CD8^+$ T cells of the 4T1-Luc tumor-bearing mice after administering the pharmaceutical composition for treating cancer and the kit for treating cancer of the present disclosure. FIG. 18A shows analysis results of the liver, FIG. 18B shows analysis results of the lung, FIG. 18C shows analysis results of the spleen, FIG. 18D shows analysis results of the kidney, and FIG. 18E shows analysis results of the colon. In FIGS. 18A to 18E, the infiltration degree of the $CD4^+$ T cells and the $CD8^+$ T cells of the group administrated with the example 3 in the liver, the lung, the spleen, the kidney and the colon are lower than that of the control group.

Figure 19A:
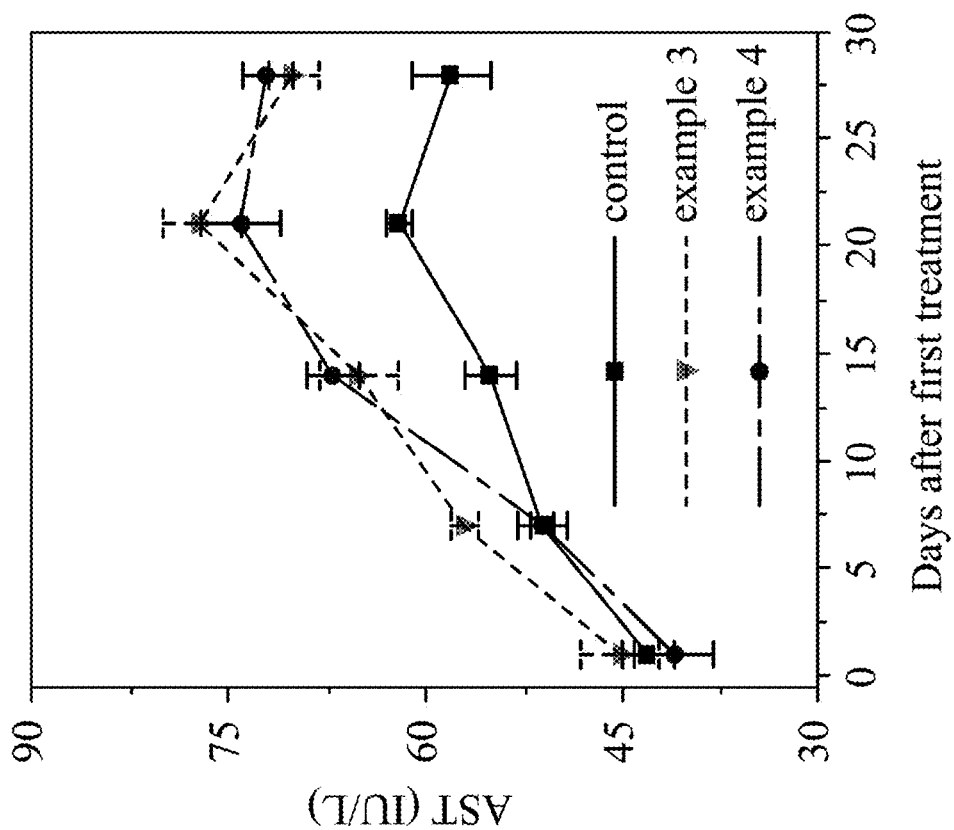
FIGS. 19A, 19B, 19C and 19D show blood biochemical analysis results of the mice after administering the pharmaceutical composition for treating cancer and the kit for treating cancer of the present disclosure.
Figure 19B:
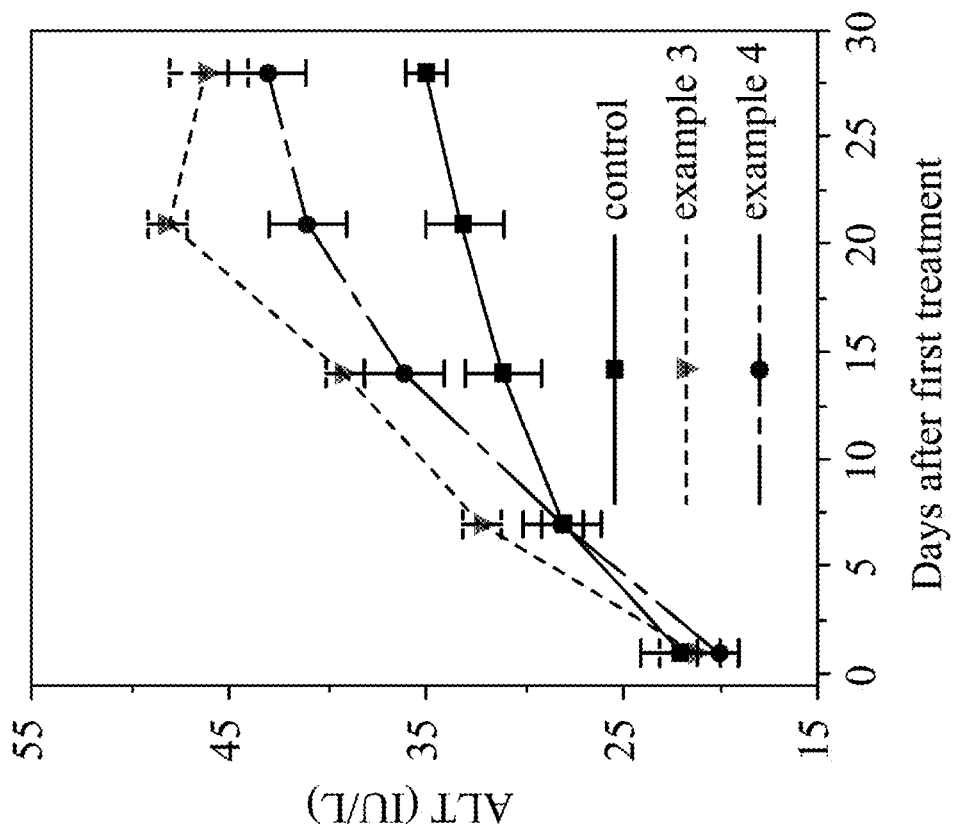
Figure 19D:
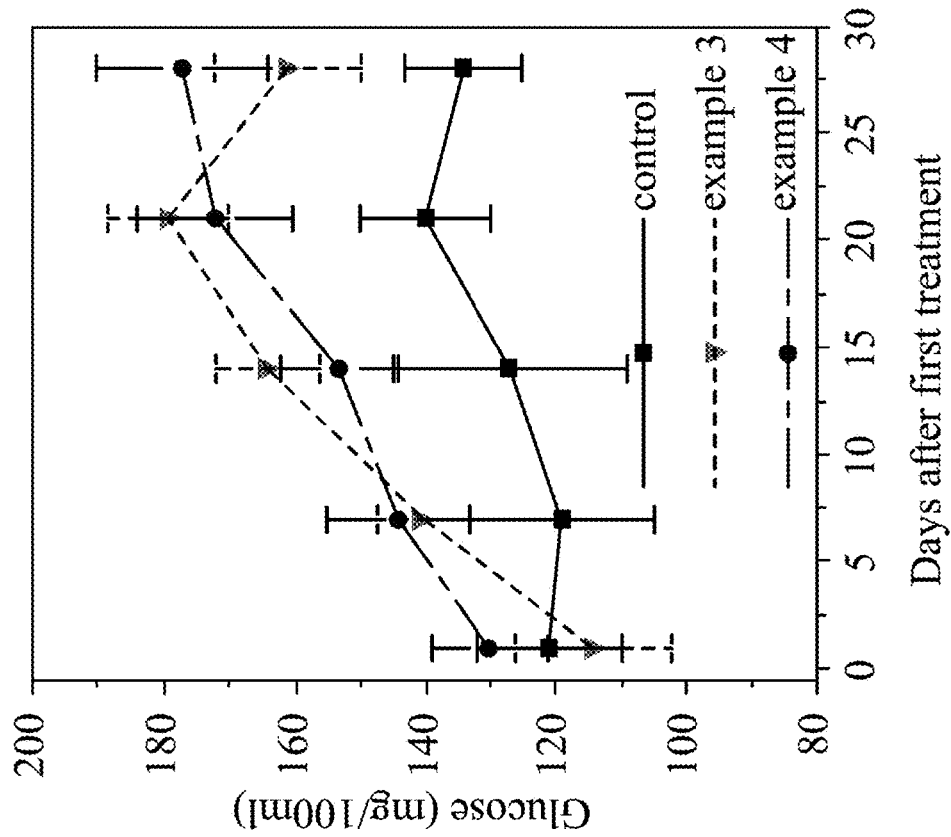
Figure 19C:
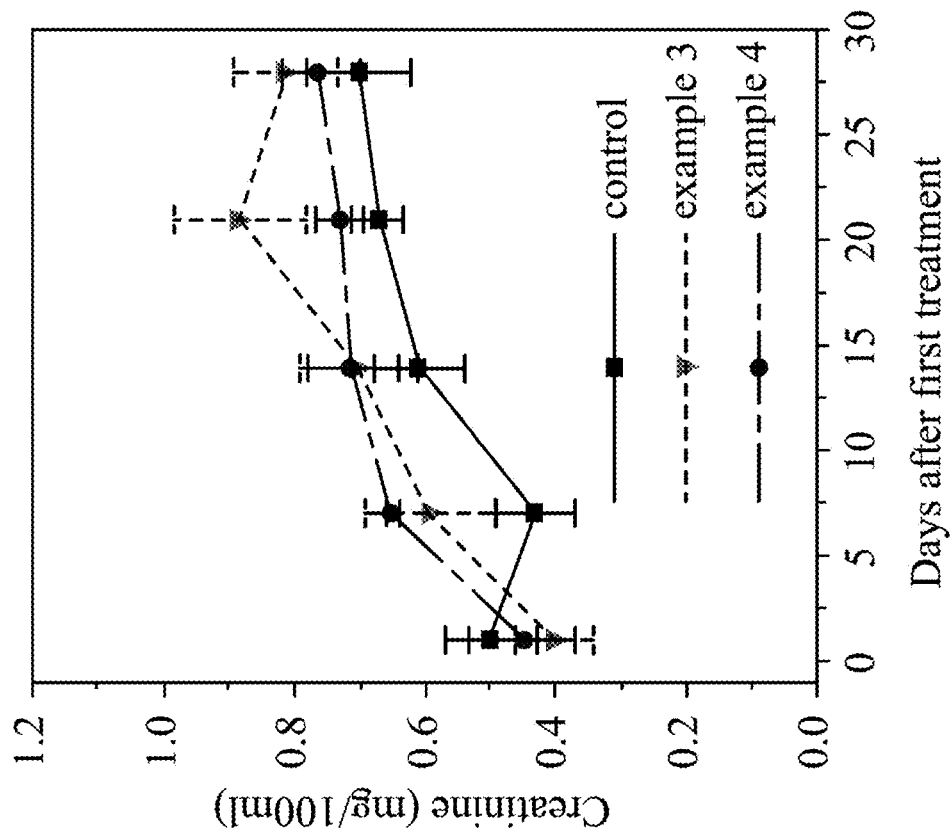

In this experiment, the effect of side effects are further determined by blood biochemical analysis to analyze the liver function index, renal function index, and blood glucose concentration, wherein the liver function index stands as the concentrations of the enzymes aspartate transaminase (AST) and alanine transaminase (ALT), and the renal function index stands as the concentration of the creatinine. Please refer to FIGS. 19A to 19D, which are blood biochemical analysis results of the 4T1-Luc tumor-bearing mice after administering the pharmaceutical composition for treating cancer and the kit for treating cancer of the present disclosure. FIG. 19A shows analysis results of AST concentration, FIG. 19B shows analysis results of ALT concentration, FIG. 19C shows analysis results of creatinine concentration, and FIG. 19D shows analysis results of blood glucose concentration. In FIGS. 19A to 19D, the blood biochemical values of the 4T1-Luc tumor-bearing mice administrated with the example 3 or the example 4 are within the normal range as the control group. These results indicate that the pharmaceutical composition for treating cancer and the kit for treating cancer of the present disclosure have biosafety.

Figure 20:
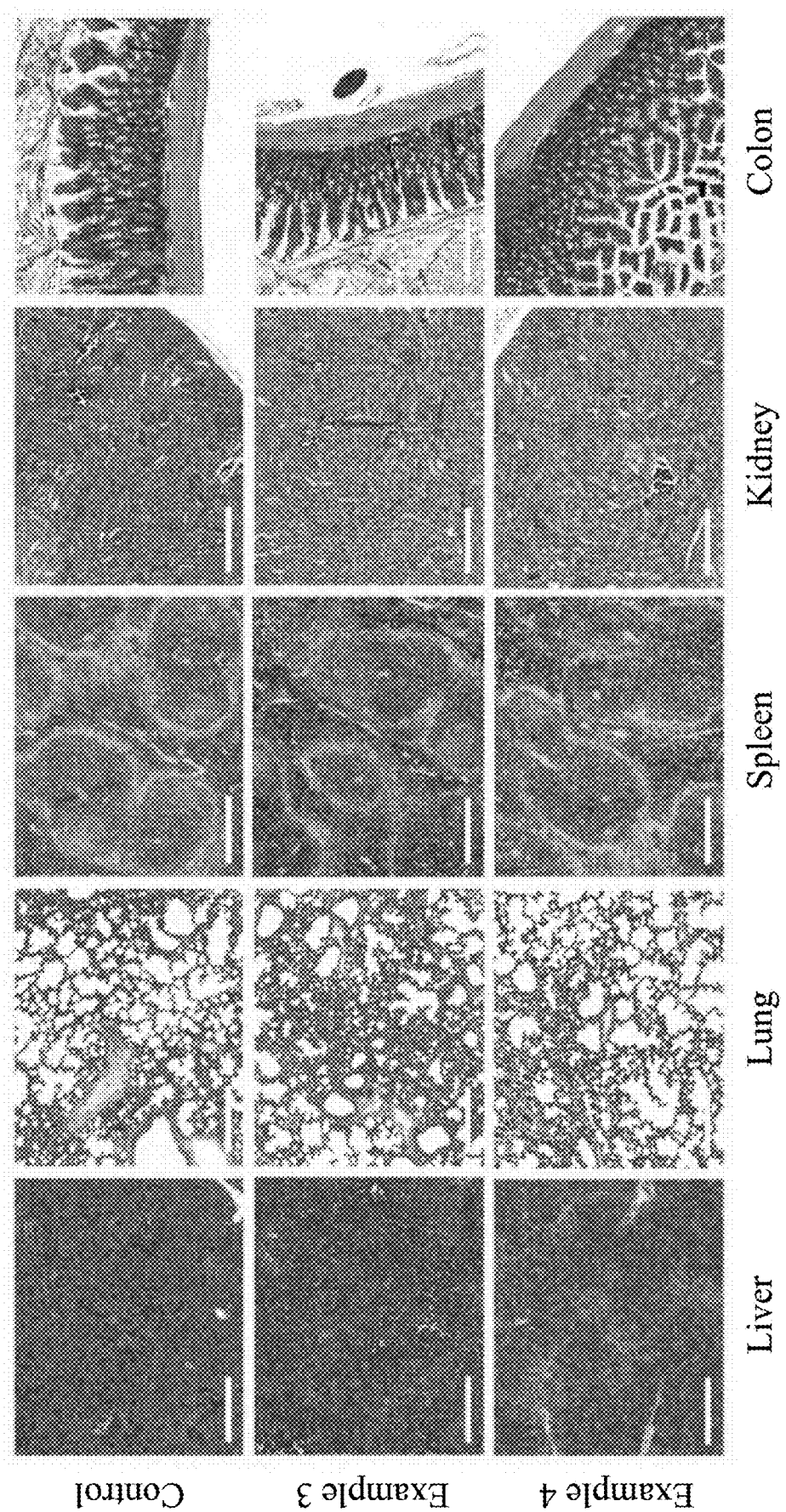
FIG. 20 are histology pictures of the mice after administering the pharmaceutical composition for treating cancer and the kit for treating cancer of the present disclosure.

In addition, the histology analysis is performed at 4 weeks after the tumor implantation. Please refer to FIG. 20, which are histology pictures of the 4T1-Luc tumor-bearing mice after administering the example 3 or the example 4. In FIG. 20, compared to the control group, there are no significant tissue damage in the liver, the lung, the spleen, the kidney, and the colon in the 4T1-Luc tumor-bearing mice administrated with the example 3 or the example 4. These results indicate that the pharmaceutical composition for treating cancer and the kit for treating cancer of the present disclosure have biosafety.

To sum up, the fabrication process of the fabrication method of the immunomagnetic nanocapsule of the present disclosure is simple. In the fabrication method of the immunomagnetic nanocapsule, the fucoidan with anticancer activity is used as the main component, and combines with the superparamagnetic iron oxide nanoparticles to form the immunomagnetic nanocapsule, which can immobilize antibody onto the outer layer and encapsulate the active substance into the core. The fabricated immunomagnetic nanocapsule is a nanoscale structure, and its size is suitable to penetrate into the tumor for enhancing the effect of the fucoidan on the tumor. The antibody immobilized onto the outer layer can be the immunosense checkpoint inhibitor and/or the T cell expansion agent, so that the immunomagnetic nanocapsule of the present disclosure can also be the immune checkpoint inhibitor and/or the T cell expansion agent in addition to the anti-cancer function of its own material for significantly improving the tumor microenvironment. Moreover, the immunomagnetic nanocapsule of the present disclosure can markedly improve the anti-cancer effect of the immunotherapy with the same antibody alone, and can achieve better tumor inhibition with less antibody dosage. The fabricated immunomagnetic nanocapsule can be lyophilized to form the powdery crystals and stored under aseptic conditions for a long period of time. The lyophilized powdery crystal can be rapidly re-dispersed in the solvent when needed, showing its convenience and stability.

The pharmaceutical composition for treating cancer includes the immunomagnetic nanocapsule and the pharmaceutically acceptable carrier. The pharmaceutical composition for treating cancer can be used for inhibiting the proliferation of cancer cells, reducing the metastasis of cancer cells and triggering the tumor immune response. The kit for treating cancer includes the immunomagnetic nanocapsule and the magnetic field generator, wherein the magnetic field generator can be the auxiliary tool to generate the magnetic field for the magnetic navigation. Thus, the immunomagnetic nanocapsule of the present disclosure in the kit for treating cancer can be accumulated in the affected part, so that the immune cells can significantly proliferate in the tumor and the immune response of the systemic circulation can be reduce for further enhancing the anti-cancer effect of the immunomagnetic nanocapsule of the present disclosure. The results of the aforementioned experiments indicate that the kit for treating cancer has the therapeutic effect of local treatment. Therefore, the kit for treating cancer of the present disclosure simultaneously has the physical target function and biological target function, which is helpful for the immunotherapy with the chemotherapy or the combination therapy of the immunotherapy, and can avoid serious side effects caused by strong immune response.

Although the present disclosure has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An immunomagnetic nanocapsule, comprising:
   a core;
   a shell formed by a complex, wherein the complex is fabricated by a combination of a fucoidan, an oxidized dextran, and a plurality of superparamagnetic iron oxide nanoparticles via a hydrophobic interaction between the fucoidan, the oxidized dextran, and the plurality of superparamagnetic iron oxide nanoparticles, and the core is encapsulated in the shell; and
   an outer layer comprising at least one antibody immobilized onto an outside of the shell to form the outer layer, wherein the antibody is an immune checkpoint inhibitor and/or a T cell expansion antibody.

2. The immunomagnetic nanocapsule of claim 1, wherein the immunomagnetic nanocapsule is a sphere with a particle size ranging from 80 nm to 350 nm.

3. The immunomagnetic nanocapsule of claim 1, wherein the fucoidan is extracted from *Undaria pinnatifida*, *Macrocystis pyrifera*, or *Fucus vesiculosus*.

4. The immunomagnetic nanocapsule of claim 1, wherein the oxidized dextran has an aldehyde group.

5. The immunomagnetic nanocapsule of claim 4, wherein the oxidized dextran is prepared from a dextran with a molecular mass ranging from 5 kDa to 270 kDa.

6. The immunomagnetic nanocapsule of claim 1, wherein the immune checkpoint inhibitor is selected from the group consisting of a PD-L1 antibody, a PD-1 antibody, a CTLA-4 antibody and a TIM-3 antibody.

7. The immunomagnetic nanocapsule of claim 1, wherein the T cell expansion antibody is selected from the group consisting of a CD3 antibody, a CD28 antibody and a 4-1BB antibody.

8. The immunomagnetic nanocapsule of claim 1, wherein the core further comprises an active substance.

9. A kit for treating a cancer, comprising:
   the immunomagnetic nanocapsule of claim 1; and
   a magnetic field generator.

10. The kit for treating the cancer of claim 9, wherein the magnetic field generator is a magnet, a three-dimensional field magnet or a magnetic resonance imaging scanner.

11. The kit for treating the cancer of claim 9, wherein the cancer is a breast cancer or a colorectal cancer.

* * * * *